US010572733B2

United States Patent
Wells et al.

(10) Patent No.: US 10,572,733 B2
(45) Date of Patent: Feb. 25, 2020

(54) AUGMENTED REALITY THERAPEUTIC MOVEMENT DISPLAY AND GESTURE ANALYZER

(71) Applicant: Zimmer US, Inc., Warsaw, IN (US)

(72) Inventors: Richard Wells, Ada, MI (US); Timothy R. Price, East Grand Rapids, MI (US); Ted Spooner, Grand Rapids, MI (US); Dave Van Andel, Spring Lake, MI (US); Travis Dittmer, Grand Rapids, MI (US); John Kotwick, Grand Rapids, MI (US); Jason Leighton, Portland, OR (US)

(73) Assignee: Zimmer US, Inc., Warsaw, IN (US)

( * ) Notice: Subject to any disclaimer, the term of this patent is extended or adjusted under 35 U.S.C. 154(b) by 116 days.

(21) Appl. No.: 15/803,515

(22) Filed: Nov. 3, 2017

(65) Prior Publication Data
US 2018/0120947 A1 May 3, 2018

Related U.S. Application Data

(60) Provisional application No. 62/440,588, filed on Dec. 30, 2016, provisional application No. 62/421,001, (Continued)

(51) Int. Cl.
*G06K 9/00* (2006.01)
*A61B 5/00* (2006.01)
(Continued)

(52) U.S. Cl.
CPC ........ *G06K 9/00671* (2013.01); *A61B 3/0033* (2013.01); *A61B 5/0002* (2013.01); (Continued)

(58) Field of Classification Search
CPC ............ G06K 9/00342; G06K 9/00671; G06T 19/006; G16H 20/30; A61B 2505/09
(Continued)

(56) References Cited

U.S. PATENT DOCUMENTS

| 8,888,721 B2 | 11/2014 | Gettelman et al. |
| 2011/0054870 A1 | 3/2011 | Dariush et al. |

(Continued)

FOREIGN PATENT DOCUMENTS

| CN | 110121748 A | 8/2019 |
| WO | WO-2013090554 A1 | 6/2013 |

(Continued)

OTHER PUBLICATIONS

"International Application Serial No. PCT/US2017/059991, International Search Report dated Jan. 4, 2018", 3 pgs.
(Continued)

*Primary Examiner* — Charlotte M Baker
(74) *Attorney, Agent, or Firm* — Schwegman Lundberg & Woessner, P.A.

(57) ABSTRACT

Systems and methods for displaying augmented reality clinical movements may use an augmented reality device to display aspects of a clinical movement. The systems and methods may use a motion capture device to capture the clinical movement. A method may include analyzing information about the clinical movement to determine a path of motion representative of at least a portion of the clinical movement. The method may automatically define a path region or a virtual target in an augmented reality environment overlaid on a real environment. The method may display the path region or the virtual target on an augmented reality display.

20 Claims, 9 Drawing Sheets

Related U.S. Application Data filed on Nov. 11, 2016, provisional application No. 62/416,869, filed on Nov. 3, 2016.

(51) Int. Cl.

| | |
|---|---|
| *G02B 27/00* | (2006.01) |
| *G02B 27/01* | (2006.01) |
| *G06F 19/00* | (2018.01) |
| *G06T 19/00* | (2011.01) |
| *A61B 3/00* | (2006.01) |
| *G06F 3/01* | (2006.01) |
| *G06F 3/0487* | (2013.01) |
| *G06Q 50/22* | (2018.01) |

(52) U.S. Cl.
CPC ....... *G02B 27/0093* (2013.01); *G02B 27/017* (2013.01); *G02B 27/0176* (2013.01); *G06F 3/017* (2013.01); *G06F 3/0487* (2013.01); *G06F 19/3418* (2013.01); *G06F 19/3481* (2013.01); *G06T 19/006* (2013.01); *A61B 2505/09* (2013.01); *G06F 3/011* (2013.01); *G06Q 50/22* (2013.01)

(58) Field of Classification Search
USPC ......... 382/103; 700/246; 901/1, 47; 600/595
See application file for complete search history.

(56) References Cited

U.S. PATENT DOCUMENTS

| | | | |
|---|---|---|---|
| 2012/0108909 A1 | 5/2012 | Slobounov et al. | |
| 2012/0296235 A1 | 11/2012 | Rupp et al. | |
| 2013/0123667 A1* | 5/2013 | Komatireddy | A61B 5/0002 600/595 |
| 2014/0147820 A1 | 5/2014 | Snow et al. | |

FOREIGN PATENT DOCUMENTS

| | | |
|---|---|---|
| WO | WO-2013142069 A1 | 9/2013 |
| WO | WO-2014160172 A1 | 10/2014 |

OTHER PUBLICATIONS

"International Application Serial No. PCT/US2017/059991, Written Opinion dated Jan. 4, 2018", 8 pgs.

"U.S. Appl. No. 15/803,499, Final Office Action dated Apr. 19, 2019", 30 pgs.

"U.S. Appl. No, 15/803,499, Response filed Feb. 13, 2019 to Non Final Office Action dated Nov. 13, 2018", 10 pgs.

"U.S. Appl. No, 15/803,499, Non Final Office Action dated Nov. 13, 2018", 25 pgs.

"U.S. Appl. No. 15/803,499, Advisory Action dated Jun. 28, 2019", 2 pgs.

"U.S. Appl. No. 15/803,499, Examiner Interview Summary dated Jun. 12, 2019", 3 pgs.

"U.S. Appl. No. 15/803,499, Non Final Office Action dated Aug. 20, 2019", 34 pgs.

"U.S. Appl. No, 15/803,499, Response filed Jun. 19, 2019 to Final Office Action dated Apr. 19, 2019", 11 pgs.

Mine, M R, et al., "Moving Objects in Space: Exploiting Proprioception in Virtual-Environment Interaction", [Online] Retrieved from the internet: <https://web.archive.Org/web/20070417131910/https://www.cs.unc.edu/~walk/papers/mine/minecows.pdf>, (2007), 8 pgs.

\* cited by examiner

AUGMENTED REALITY THERAPEUTIC MOVEMENT DISPLAY AND GESTURE ANALYZER

CLAIM OF PRIORITY

This application claims the benefit of U.S. Provisional Patent Application Ser. No. 62/416,869, filed on Nov. 3, 2016, and claims the benefit of U.S. Provisional Patent Application Ser. No. 62/421,001, filed on Nov. 11, 2016, and claims the benefit of U.S. Provisional Patent Application Ser. No. 62/440,588, filed on Dec. 30, 2016, the benefit of priority of each of which is claimed hereby, and each of which are incorporated by reference herein in its entirety.

BACKGROUND

Telerehabilitation systems are typically used to remotely assess or monitor patients engaged in rehabilitation activities. Current telerehabilitation systems are often limited or not used for occupational or physical therapy due to the remote nature of telerehabilitation. Occupational or physical therapy includes exercises or activities to recover from an injury, surgery, or to otherwise improve mobility. Often, patients forget how to do activities associated with rehabilitation or are unable to understand the provided instructions describing the activities.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
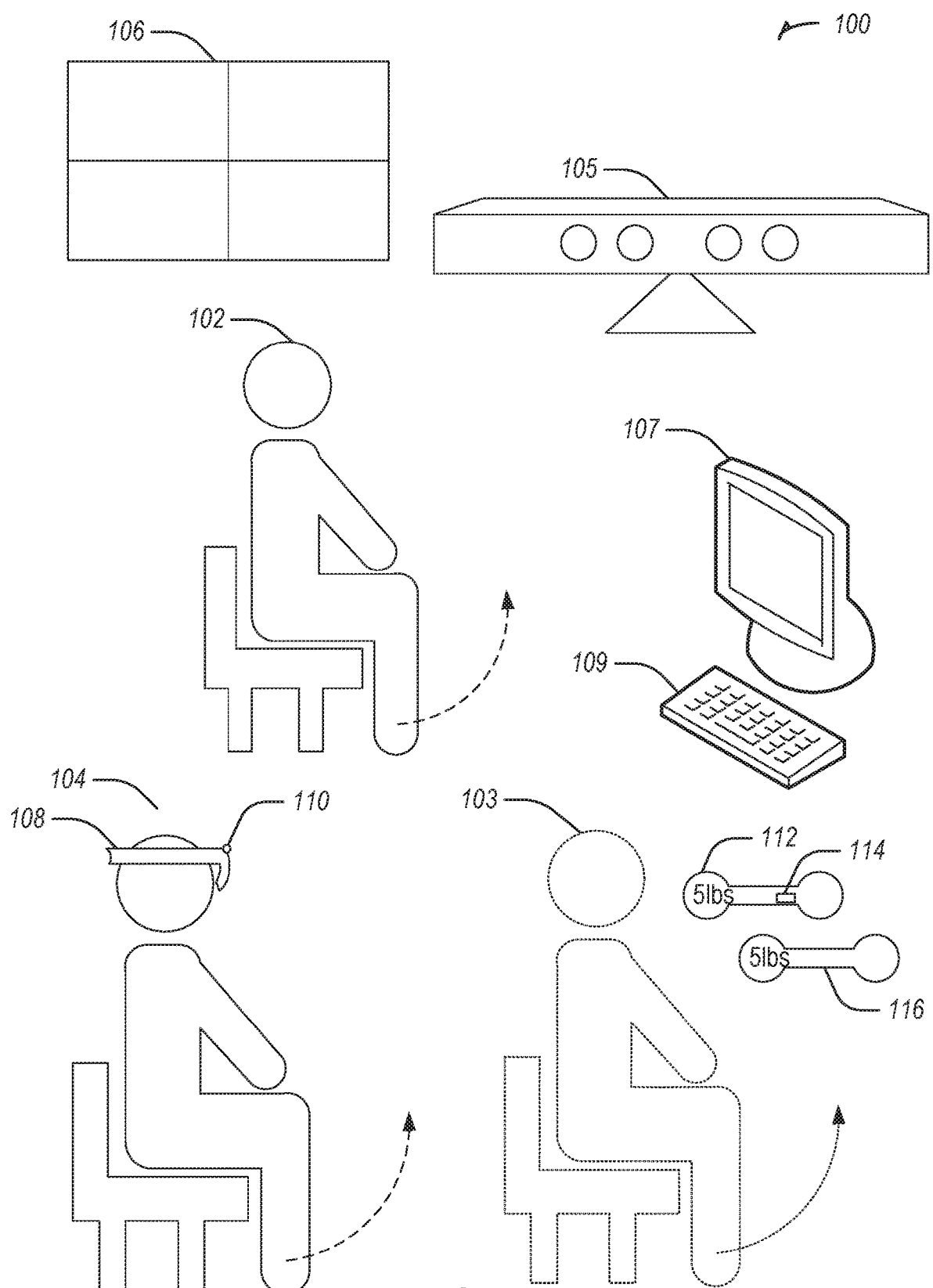
FIG. 1 illustrates real and virtual aspects of an augmented reality and exercise creation system in accordance with some embodiments.

Systems and methods for telerehabilitation feedback are described herein. The systems and methods herein describe using a movement capture apparatus to capture telerehabilitation information from a therapist or patient. The telerehabilitation systems and methods may use a user interface or video display, an augmented reality (AR) display, a virtual reality (VR) display, audible alerts, haptic feedback, a non-contact alert, or the like to present feedback.

In an example, a telerehabilitation system may be used to provide a mechanism that captures video of a rehabilitation exercise and automatically determines key points on a therapist performing the exercise in the video. The key points may be used to create visual targets, of the exercise, for a patient when the patient is attempting to perform the exercise. The system may demonstrate a rehabilitation exercise virtually, including the visual targets. The visual targets may include a "bubble," such as a spherical or circular visual representation that may be "popped" (e.g., by showing an animation or visual effect removing the bubble from display when the patient or an object interacts with the bubble). The system may capture video of the patient performing the exercise, and may analyze the patient's attempt. The visual targets may be used to display the effectiveness of the patient's attempt, for example popped bubbles may represent a successful completion of the exercise or parts of the exercise. The system may provide feedback to the patient (e.g., the popped bubbles or un-popped bubbles).

The systems and methods described herein may automatically determine a placement for a gesture bubble (e.g. a bubble placed for a gesture, such as a beginning of a gesture or an end of a gesture for an exercise), such as based on therapist movements. For example, a therapist may stand in front of a movement capture apparatus (e.g., a sensor, a sensor array, a camera, an infrared camera, two or more cameras, a depth camera, etc.) and perform a motion, and the system may automatically place a gesture bubble. The system may place the bubble in the determined location, and proceed to a second bubble. For example, a first bubble may correspond with a first location (e.g., a starting location), and a second bubble may correspond with a second location (e.g., an ending location). A path region may include a path between the first location and the second location, or may include the starting location or the ending location. In an example, a gesture video may be created using the path region, one or more bubbles, captured video from a therapist, captured video from a patient, an animation segment, or the like. In an example, a gesture may include a movement in an exercise, or may be an exercise (e.g., a gesture may include a movement with multiple movements making up an exercise, or a gesture may include a movement of an exercise, which may be repeated or include other gestures or exercises to form a routine).

Augmented reality (AR) is a technology for displaying virtual or "augmented" objects or visual effects overlaid on a real environment. The real environment may include a room or specific area, or may be more general to include the world at large. The virtual aspects overlaid on the real environment may be represented as anchored or in a set position relative to one or more aspects of the real environment. For example, a virtual object may be configured to appear to be resting on a table. An AR system may present virtual aspects that are fixed to a real object without regard to a perspective of a viewer or viewers of the AR system. For example, a virtual object may exist in a room, visible to a viewer of the AR system within the room and not visible to a viewer of the AR system outside the room. The virtual object in the room may be displayed to the viewer outside the room when the viewer enters the room. In this example, the room may act as a real object that the virtual object is fixed to in the AR system.

An AR system may be viewable to one or more viewers, and may include differences among views available for the one or more viewers while retaining some aspects as universal among the views. For example, a heads-up display may change between two views while virtual objects may be fixed to a real object or area in both views. Aspects such as a color of an object, lighting, or other changes may be made among the views without changing a fixed position of at least one virtual object.

A user may see a virtual object presented in an AR system as opaque or as including some level of transparency. In an example, the user may interact with the virtual object, such as by moving the virtual object from a first position to a second position. For example, the user may move an object with his or her hand. This may be done in the AR system virtually by determining that the hand has moved into a position coincident or adjacent to the virtual object (e.g., using one or more cameras), and causing the virtual object to move in response. Virtual aspects may include virtual representations of real world objects or may include visual effects, such as lighting effects, etc. The AR system may include rules to govern the behavior of virtual objects, such as subjecting a virtual object to gravity or friction, or may include other predefined rules that defy real world physical constraints (e.g., floating objects, perpetual motion, etc.).

Systems and methods for augmented reality (AR) telerehabilitation are described herein. The systems and methods herein describe using AR to display a virtual target for a patient to allow the patient to complete a clinical movement. In an example, a virtual therapist may be displayed. In another example, a real therapist may be displayed with an AR augmentation, such as highlighting of a body part, virtual directions, etc. The virtual therapist or the real therapist may demonstrate the clinical movement. The clinical movement may include the use of an object. In an example, the AR may be used to display objects to be used by the patient. In an example, the AR may be used to display directions for a patient to perform a clinical movement. The real therapist may, for example, be a live therapist appearing with a patient, or may be a video recording of a therapist. The real therapist may be defined as any therapist that is not virtual.

The systems and methods described herein may provide overlaid virtual graphics to assist in a user's understanding of how to perform a movement. A path or target may be highlighted, a virtual representation of a patient or therapist may be shown performing the movement (e.g., overlaid on the user—as a point-of-view technique to show the movement). A virtual target may be used to aid a patient in visualizing a range to the movement (e.g., an ultimate end point for the movement).

FIG. 1 illustrates real and virtual aspects of an augmented reality and exercise creation system 100 in accordance with some embodiments. In an example, the system 100 includes a video capture device 105, a display device 107, and an input device 109 that can be used by the therapist 102 to generate model exercises for a rehabilitation patient. The therapist 102 may perform an exercise, which is captured by the video capture device 105 and displayed in the display device 107. The input device 109 may be used to edit or augment the displayed exercise, or to select one or more exercises for a routine. The system 100 may automatically edit the captured video to remove extraneous portions that come before or after the exercise performed by the therapist 102. In an example, a series of exercises may be performed by the therapist 102 and captured by the video capture device 105, and the system 100 may split the captured video of the series of exercises into individual exercise videos. In an example, the video capture device 105 may be a Kinect from Microsoft of Redmond, Wash.

Aspects of the exercise may be selected using the input device 109. The selected aspects may include a starting position, an ending position, or a transition motion. When a starting position is selected, the display device 107 may display the selection at the appropriate time in the captured video of the exercise. For example, a circle may be drawn around a displayed body part (e.g., a foot, a hand, etc.), which may be displayed in the captured video for the exercise. Similarly, an ending position may be highlighted. When a transition motion is selected, a path may be displayed during the captured video that tracks with the selection. The starting position, ending position, or the transition motion may include more area on the captured video than the body part occupies (e.g., a radius around a center point of the body part).

In an example, the system 100 may be calibrated using the video capture device 105. The video capture device 105 may use infrared light to detect the therapist 102 in a field of view. The system 100 may evaluate the detection to identify joints, limbs, appendages, a head, etc., of the therapist 102. These identified body parts may be used with later captured video of an exercise to label specific body parts.

After a video of an exercise is captured by the video capture device 105, the therapist 102 (or another user) may edit the captured video. In an example, the therapist 102 may select portions of a captured video and add tags, such as "introduction," "exercise," "first repetition," "second repetition," "outro," or the like. In an example, a single repetition captured may be repeated in an edited video to show multiple repetitions for patient viewing.

A final edited video may be created for an exercise. The final edited video may be named and given a category tag, such as a body part, a muscle group, a post-surgery type designation, a patient-specific tag, or the like. The final edited video may be saved for later use in constructing a routine, such as by the therapist 102. In another example, the final edited video may be saved to a database to be shared with other users (e.g., other users caring for a patient shared with the therapist 102, other therapists in a company, group, or hospital, publicly, or the like). In an example, the system 100 may be used to repeat an exercise a specified number of times so that a patient may view the exercise the specified number of times to complete a routine, or part of a routine.

The system 100 may be used to capture three-dimensional movement. For example, the video capture device 105 may include a movement capture apparatus. The movement capture apparatus may include two or more infrared sensors or cameras to detect or capture three dimensional movement. The video capture device 105 may include a camera to capture video in conjunction with infrared captured movement. The movement captured may include video.

The system 100 may interact with a real therapist (e.g., therapist 102), or may include a virtual therapist 103 displayed within the system 100. The system 100 may be used by a patient 104. The system 100 includes an AR device 108. In an example, the system 100 may include a reference wall 106, a physical object 112, a virtual object 116, or a camera 110. In an example, the physical object 112 may include a sensor 114. In another example, a sensor may be embedded on an implant of the patient 104. In an example, the camera may be coupled to the AR device 108. The AR device 108 may include a headset, glasses, goggles, contacts, a projector, or the like. In an example, the reference wall 106 may be identified during configuration or calibration of the AR device 108.

The AR device 108 may include the camera 110. The camera 110 may include an infrared camera, an infrared filter, a visible light filter, a plurality of cameras, a depth camera, etc. The AR device 108 may project virtual items over a representation of a real environment, which may be viewed by the patient 104. In an example, the real environment may include display of a floor, a room, and physical props, among other things. The therapist 102 may be present in the real environment, and virtual aspects may be overlaid on the therapist 102 within the AR environment generated by the AR device 108. In another example, the virtual therapist 103 may include virtual aspects, such as highlighting of body parts, movement arrows, blurring to show motion, or the like. The virtual therapist 103 may be placed in the real environment at a predetermined location, such as a location in the real environment that is within an area visible to the patient 104 or the AR device 108. For example, the virtual therapist 103 may located in front of the AR device 108 within the system 100 as visible by the patient 104, such that the patient 104 may view the virtual therapist 103. When the patient 104 turns the AR device 108, the virtual therapist 103 may be designed to disappear from view similar to how the real therapist 102 would disappear if the patient's head turned.

In an example, the virtual therapist 103 may be shown overlaid on the real environment, to demonstrate an exercise. In an example, a virtual display of props or objects, such as for use in exercise may be overlaid on the real environment. For example, the virtual object 116 may represent the physical object 112. The AR device 108 may be used to instruct the patient 104 to find the physical object 112 in the room by displaying the virtual object 116 as an example. In an example, the virtual object 116 may be displayed in use by the virtual therapist 103 or may be displayed adjacent to, above, or floating near, the real therapist 102.

The physical object 112 may include the sensor 114. The sensor 114 may be used to track patient progress, such as a duration or number of repetitions completed by the patient 104. In an example, the sensor 114 may be used to identify the physical object 112 to the AR device 108. Once identified, the AR device 108 may select the virtual object 116 that corresponds to the physical object 112. For example, if the patient 104 has a ten pound weight and a five pound weight available, these may be identified via sensors in the weights, and the AR device 108 may determine the five pound weight is to be used in an exercise, and the virtual object 116 may resemble the five pound weight. The virtual object 116 may change to resemble the ten pound weight in another exercise or when increasing weight to increase difficulty for the exercise. In an example, the AR device 108 may display a virtual movement of a limb or a virtual exercise or may display virtual bubbles for indicating a starting position, an ending position, or a path for a movement or exercise.

In an example, an implant sensor may be embedded in an implant in the patient 104. The implant sensor may be used to track movement (such as a number of repetitions), non-movement, etc., of the patient 104. This tracked movement may be used to augment movement captured by the camera 110 or a patient-facing movement capture apparatus (e.g., a sensor, a sensor array, a camera, an infrared camera, two or more cameras, a depth camera, etc.). Movement of the patient 104 may be tracked using a patient-facing movement capture apparatus, the camera 110, the implant sensor, or any of the movement capture apparatus, among other things. In an example, therapy output or therapy prescribed may be changed or updated based on sensor data from the implant sensor. For example, with a total knee arthroplasty the knee prosthesis (implant) may include a sensor to monitor pressure generated during movement, and when there is too much pressure on one side of an implant, an indication to ease the movement, change the movement, or stop the movement may be displayed using the AR device 108. The implant sensor or AR device 108 data (e.g., whether the patient 104 is successfully performing movements, a percentage of successful performance, metrics related to number of repetitions, weight used, etc., or the like) may be used by the therapist 102 or other caregiver (e.g., a surgeon) after the patient 104 performs a movement, completes a scheduled session, or performs at least part of scheduled therapy. The data may be used to adjust prescribed therapy, movement, exercises, medication, surgery timetable, or the like. The patient 104 and the real therapist 102 may be able to use the AR device 108 or multiple AR devices to share an augmented experience. For example, the real therapist 102 may have an AR device, and the AR device of the therapist 102 may display augmented and virtual aspects in a shared environment with the AR device 108, overlaid on the same real environment. The real therapist 102 may manipulate virtual or real aspects of the shared environment such that the patient 104 may see the manipulation. For example, the real therapist 102 may pop a virtual bubble or lift a virtual object, wherein the virtual bubble or the virtual object may be visible to the patient 104 and the real therapist 102, as further discussed below with respect to FIG. 2 and as described herein below in paragraph and elsewhere.

Figure 2:
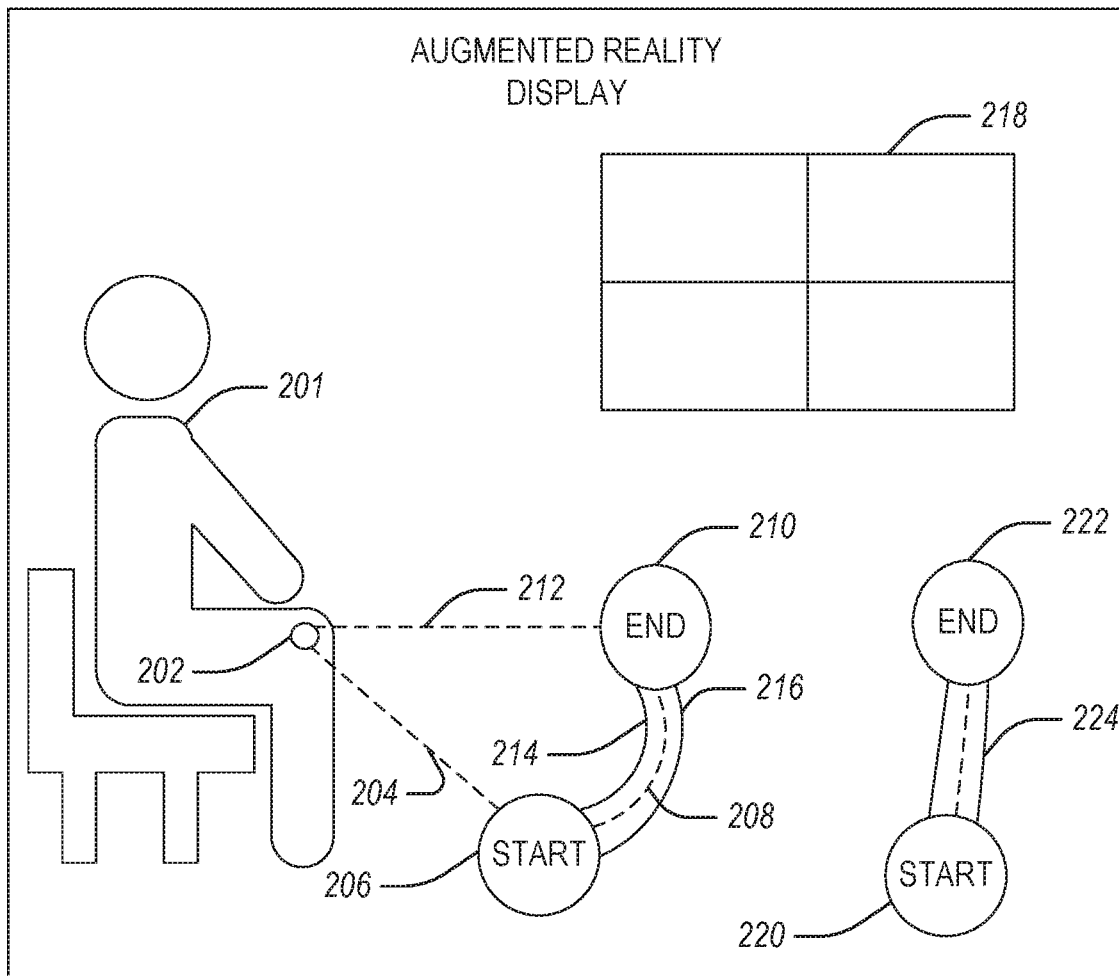
FIG. 2 illustrates an augmented reality display in accordance with some embodiments.

FIG. 2 illustrates an augmented reality (AR) display 200 in accordance with some embodiments. The AR display 200 may be used by a patient 201, to display virtual aspects in a real environment. The AR display 200 may include a virtual identification of a joint 202 of the patient 201, a reference wall 218 displayed in the real environment, or a plurality of virtual reference indications. The reference indications may include a virtual starting bubble 206, a virtual ending bubble 210, a virtual path of motion 208, virtual edges 214 and 216 to a path region, a virtual starting limb position 204, or a virtual ending limb position 212. In an example, the reference indications may include a virtual example starting bubble 220, a virtual example ending bubble 222, or a virtual example path region 224. The virtual example starting bubble 220, the virtual example ending bubble 222, or the virtual example path region 224 may be displayed overlaid within the AR environment on a representation of a therapist present in the real environment. In another example, the virtual example starting bubble 220, the virtual example ending bubble 222, or the virtual example path region 224 may be displayed overlaid on a virtual therapist. In yet another example, the virtual example starting bubble 220, the virtual example ending bubble 222, or the virtual example path region 224 may be displayed with a virtual limb (e.g., a body part of a virtual therapist without displaying an entire virtual therapist). In another example, the virtual example starting bubble 220, the virtual example ending bubble 222, or the virtual example path region 224 may be displayed without a virtual or without a therapist present in the real environment.

In an example, the virtual starting bubble 206, the virtual ending bubble 210, the virtual path of motion 208, or the virtual edges 214 or 216 to the path region may be displayed virtually. The virtual starting bubble 206, the virtual ending bubble 210, the virtual path of motion 208, or the virtual edges 214 or 216 to the path region may be displayed using a color or a plurality of changing colors, may be sequentially displayed, or the like. In an example, the virtual starting bubble 206, the virtual ending bubble 210, the virtual path of motion 208, or the virtual edges 214 or 216 to the path region may be "popped" or otherwise removed from view if the patient performs a movement corresponding to the virtual representations. For example, if the patient physically places a body part in a location occupied in the AR by the virtual starting bubble 206, the virtual starting bubble 206 may pop. In an example, the virtual path of motion 208 may include a plurality of bubbles to be popped as a body part moves from the virtual starting bubble 206 to the virtual ending bubble 210.

In an example, an AR device may be used to generate the AR display 200. The AR device may include a projection screen, goggles, glasses, etc. In an example, the AR device may project an animation around the patient 201, allowing the patient 201 to see the virtual starting bubble 206, the virtual ending bubble 210, the virtual path of motion 208, the virtual edges 214 and 216 to the path region, the virtual starting limb position 204, or the virtual ending limb position 212. When the patient 201 moves, the AR device may present an avatar, such as a virtual therapist, to present a virtual therapy experience. The virtual therapist may be preprogrammed or controlled in real time by a therapist. In an example, the patient 201 may have an opportunity to ask questions of the virtual therapist using the AR display 200 or input devices within the AR device 108. Therapy for the patient 201 may be changed based on the questions, answers, or interactions with the patient 201. For example, based on how the patient 201 interacts, exercises may decrease or increase in difficulty or duration. In an example, the patient 201 may ask the therapist to repeat or describe an exercise. The avatar may direct the patient 201 to a physical location, model an exercise, offer encouragement, correction, modification, show success or failure, or the like. In an example, the avatar may occupy a virtual physical presence, such as a static position in a room (e.g., relative to the reference wall 218).

The AR display 200 may allow the patient 201 to select a joint or location on an AR avatar. By selecting a joint or location on the AR avatar, the patient 201 may indicate what hurts or needs attention on the patient 201, select a side of the body, be prompted for a pain level, or the like. In another example, the patient 201 may select options from a user interface within the AR display 200, such as, a scale bar to select pain. The AR display 200 may include a questionnaire for the patient to answer so that a therapist may evaluate progress or determine exercises for the patient.

In an example, the patient 201 may have a personalized movement profile. The personalized movement profile may be applied by an AR device to cause the AR display 200 to be personalized. The personalized AR display 200 may include specific exercises, movements, limitations, or the like that are custom to the patient 201. For example, if the patient 201 has received an implant, such as received during a total knee arthroscopy, hip replacement, heart device implant surgery, etc., the AR display 200 may include exercises designed with these implants or surgeries in mind. The AR display 200 may include education for the patient 201, such as to improve outcomes or mitigate movement that may hurt the patient.

In an example, the AR display 200 may include a virtual mirror. The virtual mirror may be used in a mirrorboxing technique. Mirrorboxing may be used to mirror a limb, such as when a mirror limb is not present. For example, if the patient 201 has lost the left leg below the knee, the right leg may be mirrored in the AR display 200, such that the AR display 200 may display the left leg below the knee by mirroring the right leg. In another example, the left leg below the knee may be displayed virtually, based on the right leg, or constructed from virtual components. Mirrorboxing may be used to give the patient 201 relief from phantom limb pain, allow a patient to attempt to regain use of a limb, relieve pain in a limb, etc. The virtually displayed limb may be used to map movement in the brain of the patient 201, such as by superimposing the limb and instructing the patient 201 to move the limb virtually. For example, the patient 201 may not have control of the right arm and may move the left arm. When the left arm moves in the real environment, that may cause the right arm to move virtually in the AR display 200. The brain of the patient 201 may map the pathway to actually control the right arm by moving the left arm and viewing the right arm moving. This technique may be used to heal or repair the movement ability of the right arm.

Figure 3:
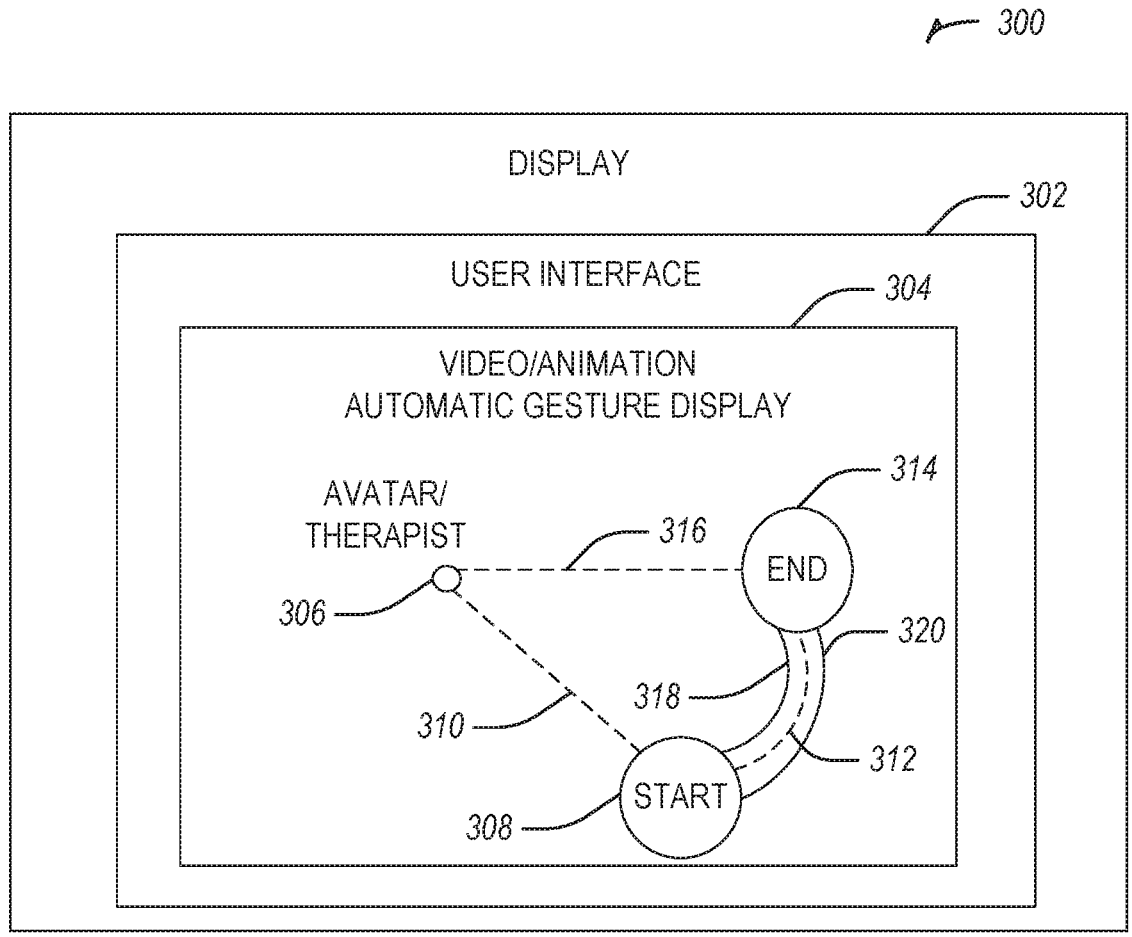
FIG. 3 illustrates an automatic gesture display system in accordance with some embodiments.

FIG. 3 illustrates an automatic gesture display system 300 in accordance with some embodiments. The automatic gesture display system 300 includes a user interface 302. The user interface 302 includes a video/animation automatic gesture display component 304. The video/animation automatic gesture display component 304 may be used to add movement bubbles (e.g., 308 or 314) or a path region, manually or automatically. In an example, movement bubbles (e.g., 308 or 314) may be added to a path of motion 312 automatically. For example, including success parameters or failure parameters may be added to the path of motion 212 to create a path region (e.g., a region around the path of motion 312 between edge 318 and edge 320). The path region may be used to show a patient how to perform the clinical movement. The path region may be used to determine whether the movement by the patient was successful. In an example, the path region or the path motion may be displayed on a display (e.g., a screen, an AR display, a VR display, etc.).

In an example, the path region may be used to determine whether a patient has successfully completed an exercise. For example, if the patient completes the exercise within the path region, the exercise may be determined to be completed successfully. If the patient moves outside the path region while attempting to complete the exercise, the exercise may be determined to not be completed successfully. In another example, the movement bubbles may be used to analyze a patient video to determine if the patient has properly performed the exercise. For example, if the patient is able to pop the bubbles (e.g., all the bubbles in an exercise), exercise while performing an exercise, the exercise may be determined to be completed successfully. In an example, the exercise may be partially completed if one or more bubbles are popped. In another example, the path region and the bubbles may be used to determine if the exercise has been completed successfully.

The path region may be represented in two dimensions or three dimensions. For example, the path region may include a two dimension expansion of the path of motion 312. In another example, the path region may include a three dimension expansion of the path of motion 312. For example, the path region may include an area within a radial distance (e.g., in two or three dimensions) away from the path of motion 312. In an example, a starting position or an ending position may be indicated for the path of motion 312. The starting position or the ending position may include a radial distance (e.g., two or three dimensional) away from a starting point or ending point of the path of motion 312 respectively. For example, the starting position may include a circle or sphere around the starting point of the path of motion 312. The starting point may be indicated by a therapist or may be detected automatically.

The video/animation automatic gesture display component 304 includes a start bubble 308 at a starting location (e.g., corresponding to the starting location 208 of FIG. 2) and an end bubble 314 at an ending location (e.g., corresponding to the ending location 214 of FIG. 2). The video/animation automatic gesture display component 304 includes a captured video displayed or animated joint 306, and limb locations 310 and 316 corresponding to a start and an end respectively. The video/animation automatic gesture display component 304 may automatically generate the start bubble 308, the end bubble 314, the edge 318, or the edge 320. In an example, the edges 318 and 320 may be automatically generated at a predetermined distance from the path of motion 312 (e.g., a number of pixels, a distance determined using a scaling of captured video or an animation distance).

In an example, a clinical movement captured from a therapist may be later animated and the animation may be used with a path region to create a gesture video. In another example, a therapist may select a previously generated animation to create a gesture video. In another example, a therapist may select a previously captured video to create a gesture video. To create a gesture video, a therapist may select a joint that moves (e.g., joint 306), for example a knee joint, a hip joint, an elbow joint, a shoulder joint, a neck joint, etc. The joint 306 may be automatically detected in a captured video, and a path region may be applied to movement extending from the joint 306 (e.g., if a knee joint is selected, the path region may be for the foot as it travels while the knee joint is extended, or, in another example, the selected joint may be used as the path region), such as along the path of motion 312 between the edges 318 and 320 from the start bubble 308 to the end bubble 314.

In an example, a movement capture apparatus may be used to capture video and the start bubble 308 and the end bubble 314 may be automatically added to the captured video. The start bubble 308 or the end bubble 314 may be color coordinated, such as a green start bubble 308 indicating the starting point for a movement and a red end bubble 314 indicating the ending point for the movement. In an example, the colors may change as the movement is in progress. For example, the start bubble 308 may be a first color and then change as a specific body part or object is placed within the start bubble 308, upon which the start bubble 308 may change to a second color to indicate the placement is correct. The edges 318 or 320 may similarly change color based on whether movement is within or outside the edges 318 or 320. The end bubble 314 may similarly change color when the body part or object is placed in the end bubble 314. In an example, the start bubble 308 or the end bubble 314 may be "popped" (e.g., animated to disappear), such as when a user places a body part or object (e.g., a predetermined specific body part or object) within the start bubble 308 or the end bubble 314. In an example, a series of bubbles may be placed between the start bubble 308 and the end bubble 314, such as along the path of motion 312. The series of bubbles may change color or pop as described above for the start bubble 308 or the end bubble 314. In another example, the start bubble 308 and the end bubble 314 may be in the same place or near each other. For example, the path of motion 312 may include a round trip or movement away from the start bubble 308 and then back towards or near the start bubble 308, which may transition during the movement to being the end bubble 314.

In an example, a therapist may select a gesture flag to identify joints that the patient must move in order to satisfy the exercise conditions. A movement capture apparatus may be used to determine whether the motion is captured and whether the identified joints are moved in the way indicated by the gesture flag(s). For example, a gesture flag selected by the therapist may correspond to a joint tag identified by the movement capture apparatus.

In an example, bubbles may be used to indicate a restriction on movement. For example, a particular movement may include a limit on head movement to within a certain bubble to ensure that the patient correctly performs the movement.

The user interface 302 of FIG. 3 may be used as a video/animation creation display system in accordance with some embodiments. The user interface 302 may include a video/animation creation component. The movement may be done along a path of motion 312. The video/animation creation component may be used to edit or display captured video, edit or display animation, or edit or display a location or a path of motion, such as an automatically generated location or path of motion. In an example, a therapist may record a clinical movement using a movement capture apparatus, such as an infrared sensor or a camera. The recording may use a plurality of cameras. The recorded clinical movement may be analyzed to determine the path of motion 312.

The automatic gesture display system 300 may include an AR authoring tool. The AR authoring tool may be used to augment aspects of a detected gesture or clinical movement. For example, the AR authoring tool may be used to change gestures or movements. In an example, the AR authoring tool may be used to create multiple different views for a gesture or movement. In another example, the AR authoring tool may be used to augment parts of a path of motion or a target object. For example, the path of motion may be augmented with a color, a distance from a center of the path of motion may be selected (e.g., to expand or contract a region around the path of motion), or set waypoints along the path of motion to indicate or identify progress along the path of motion. The target object may be augmented with a shape, color, style (e.g., flashing, pulsing, shimmering, or the like), transparency, etc.

In an example, an augmented reality device is used by a patient to see a three-dimensional animation rendered in an augmented reality display. For example, the animation may include a virtual representation of a therapist performing a clinical movement in an augmented reality environment overlaid on a real environment. In another example, the animation may be a virtual reality animation. In another example, the animation may be an augmented animation enhancing a clinical movement performed by a therapist in front of the patient in a real environment. For example, the therapist's arm or leg or other movement limb may be augmented, such as with a color, outline, arrow, etc., and enhanced while the therapist performs a clinical movement.

In an example, creating a path of motion or a target object may be automated with a target range of motion, such as one based on a diagnosis. For example, a therapist may perform a complete clinical movement, which may include one or more waypoints along the complete clinical movement, the waypoints representing progress points. The waypoints may include an initial partial clinical movement corresponding with a first target object along the path of motion, a second partial clinical movement corresponding with a second target object along the path of motion, etc. An ultimate target may be placed at the end of the path of motion. In this way, a plurality of path of motion targets may be established representing a full range of motion. The full range of motion may be broken down into partial range of motion segments, which may be displayed (e.g., progressively) to a patient in an augmented reality environment. The segments may be coupled to increase the range of motion targets progressively (e.g., each day adding another target with a wider range of motion). The range of motion may include functional measures that may be achieved by a patient. In an example, the range of motion may be changed based on a patient's height, weight, range of motion, proportionality, etc.

In an example, creating a path of motion or a target object may include automation, such as based on expected experiences at home, in the clinic, at work, etc. For example, a pet, slippery rug, or other activities performed by a patient in daily life may be automatically added to the augmented reality environment to reflect everyday activities in a therapeutic setting. These expected experiences may include canned protocols that may be manipulated individually, or may be from a database of common activities.

In an example, complex paths may be created by a therapist for a patient. For example, multi-step movements may be created with specific waypoints for the patient to stop at during the movements. For example, a complex path may include a first path ending at a first waypoint where the patient raises an arm up 90 degrees, and then a second path ending at a second waypoint where the patient moves the arm 90 degrees out. Paths may be created separately and added together by the therapist to create a complex path, or a complex path may be created as a step by step process.

Figure 4:
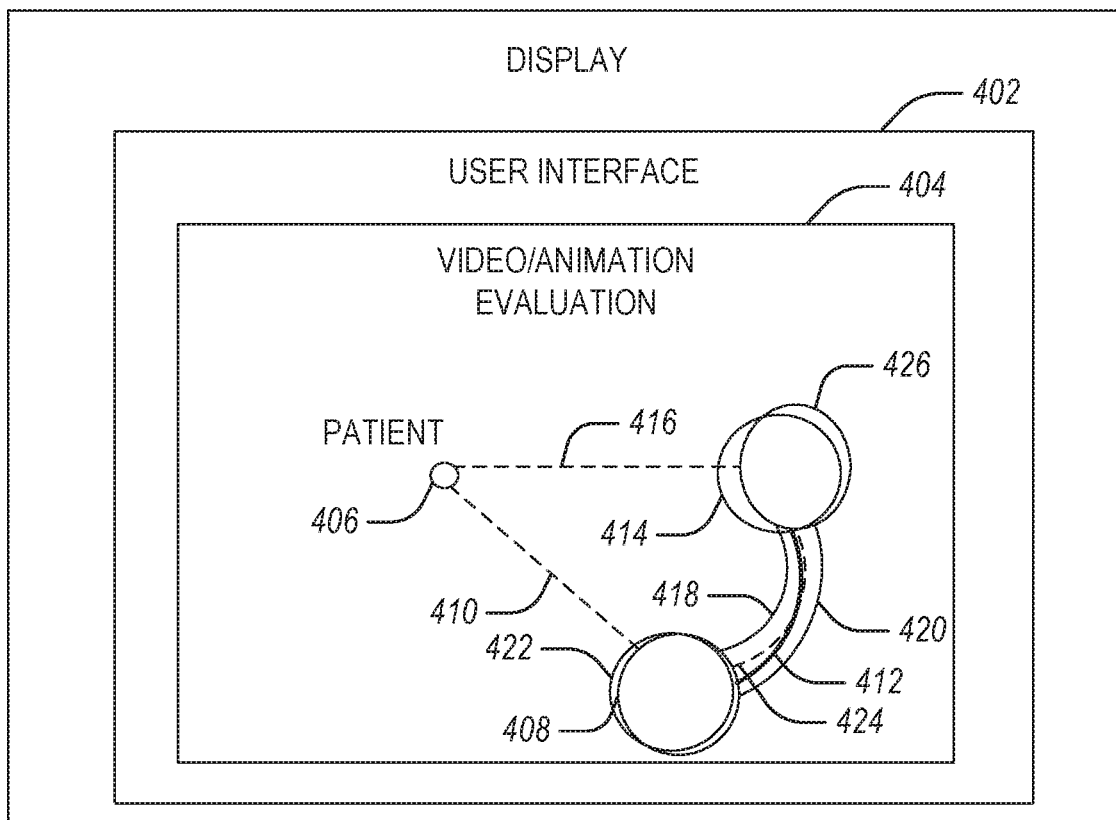
FIG. 4 illustrates a patient evaluation display system in accordance with some embodiments.

FIG. 4 illustrates a patient evaluation display system 400 in accordance with some embodiments. The patient evaluation display system 400 includes a user interface 402. In an example, the user interfaces 202, 302, and 402 may be a single user interface with different views. In another example, the user interfaces 202, 302, and 402 may be accessed using credentials, the credentials allowing access to one or more of the user interfaces 202, 302, and 402, and optionally denying access to one or more of the user interfaces 202, 302, or 402. The user interface 402 includes a video/animation evaluation component 404. The video/animation evaluation component 404 includes a joint 406 of a patient (e.g., using captured video of a patient or a live recording of a patient), and limb locations at a start 410 and an end 416. The video/animation evaluation component 404 includes an actual path the patient performed, with an actual starting location 408, an actual ending location 414, and an actual path of motion 412. The video/animation evaluation component 404 includes an intended path for the patient, with an intended starting location 422 (e.g., the start bubble 308 of FIG. 3), an intended ending location 426 (e.g., the end bubble 314 of FIG. 3), and an intended path of motion 424 (e.g., the path of motion 312). The intended path may include intended edges 418 and 420 of an intended path region. In an example, if the actual path of motion 412 falls between the intended edges 418 and 420, the patient's attempt at a clinical movement may be determined to be successful. In another example, if the actual path of motion 412 falls outside the intended edges 418 and 420, the patient's attempt at a clinical movement may be determined to be a failure. In another example, some amount of error may be tolerated, such as a brief movement outside the intended edges 418 and 420.

In an example, the actual starting location 408 may be compared with the intended starting location 422. If the actual starting location 408 aligns with the intended starting location 422, falls within the intended starting location 422, overlaps the intended starting location 422, etc., the actual starting location 408 may be determined to be successful. A similar alignment determination may be made for the actual ending location 414 and the intended ending location 426.

With a gesture video, either previously created and selected, or a newly created gesture video, a corresponding path region (e.g., enclosed by edges 418 and 420) may be determined for a patient. For example, a video of a therapist moving a joint may include a starting location, a path region, and an ending location. The therapist may differ in size from a patient, and the starting location, the path region, or the ending location may be automatically adjusted for the patient to fit the size of the patient. The starting location, the path region, and the ending location may be converted into the intended starting location 422, the intended path of motion 424, and the intended ending location 426 respectively, such as using the therapist size or the patient size. For example, if the therapist is short and the patient is tall, and the video shows the therapist raising an arm overhead, the patient's arm may raise to a higher height. The ending location may be moved to this higher height automatically based on detecting the patient's size. The therapist's size may be automatically detected, and may be stored with the video. In an example, the size of the starting location, the path region, or the ending location may be changed. These changes to locations or sizes may be done automatically and may be proportional changes such that the motion to be done by the patient is similar to the motion done by the therapist.

In an example, the patient evaluation display system 400 may be used to automatically detect or identify an orientation of a patient to a movement capture apparatus. The orientation may be compared to an orientation of captured video or animation used to display an exercise. For example, the patient may be instructed using the user interface 402 to turn a specified number of degrees, sit down, stand up, etc., so that the patient is in a correct starting position. In another example, one or more starting bubbles (e.g., the intended starting location 422) may be used to direct the patient to a starting position. For example, the intended starting location 422 may be used as an initial placement for a body part to be moved during the exercise. Additional starting locations may be used, such as a head location, torso location, leg location, arm location, or the like, or a visual indication such as a directional arrow may be displayed to provide a starting orientation for the patient to begin the exercise. In another example, the orientation of the patent may be identified and the displayed video or animation may be rotated to correspond with the orientation of the patient.

In an example, the intended starting location 422, the intended path of motion 424, the intended ending location 426, or other bubbles may be changed automatically. For example, the bubbles may be changed to create a next level, such as to increase stress, increase challenge for the patient (e.g., by moving the bubbles further away from patient, changing the exercise, etc.). The automatic adjustments may be made based on a progression, such as a progression preselected by a therapist. In an example, a therapist may select a starting point and an ending point, and the video/animation evaluation component 404 may automatically interpolate points in between to adjust bubbles to change the way that the patient proceeds. For example, the progression may be based on a unique starting point of the patient's current success or current movement pattern (e.g., level of activity), and then may automatically create the intended path of motion 424 to get to a patient's unique finish goal or intermediate goal. In an example, difficulty of intended motion may be changed, for example by changing position of the bubbles, changing bubble sizes, changing the angle between the intended starting location 408 and the intended ending location 426 from the joint 406, or the like.

In an example, the video/animation evaluation component 404 may show video captured or live of a patient performing a movement. The video captured may show reps done by the patient (e.g., automatically determined based on the bubbles being activated, reached, popped, etc.), duration, heart rate, or the like. The video capture may include a skeleton of the patient or the patient, and may black out any other background. In another example, a patient may self-report reps or duration.

In an example, the augmented reality device 501 may be used to display one or more previous attempts by a patient at performing a clinical movement. For example, the camera 506 may capture the patient performing the clinical movement for a first time, including a first range of motion (e.g., up to a first target object or a first patient-specific waypoint). The first clinical movement attempt may be stored in the memory 504 or the database 511. Then, for example when the patient attempts the clinical movement a second or later time, the first attempt may be shown to the patient in the augmented reality display 510. The one or more previous attempts by the patient may be shown with a particular effect, such as a ghosting effect (e.g., faded, dim, or ethereal). The previous attempts may be shown in the augmented reality display 510 as the patient attempts the clinical movement at the later time, (e.g., previous attempts shown in real-time with the patient attempting the clinical movement). In another example, the previous attempts may be shown on the display 510 to a therapist to show progress by a patient. In an example, attempts that are more remote in time to the present time may be shown fainter. In another example, the previous attempts may be color coded or numbered. In an example, a before and after overlay may be used by the therapist to display to the patient the progress that the patient is making with range of motion on the clinical movement. The previous attempts may be shown to the patient using a first person view, displaying a range of motion with progression that may be personalized to the patient.

Figure 5:
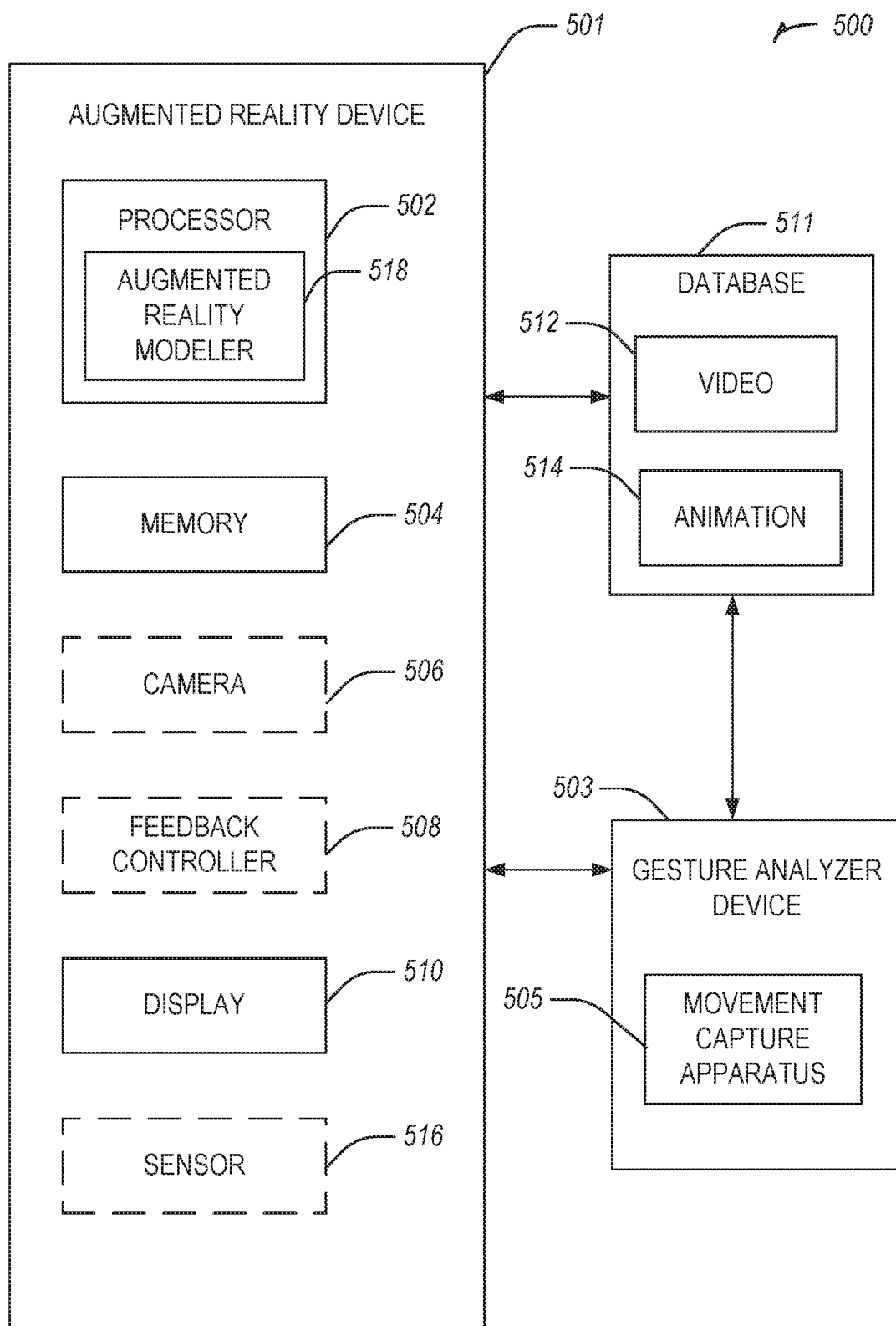
FIG. 5 illustrates a telerehabilitation system in accordance with some embodiments.

FIG. 5 illustrates a system 500 for displaying augmented reality clinical movements in accordance with some embodiments. The system 500 includes a gesture analyzer device 503. The gesture analyzer device 503 may include a processor and memory or may be connected to a device, such as the augmented reality device 501 that includes a processor 502 and memory 504. In an example, the gesture analyzer device 503 may include a movement capture apparatus (e.g., a camera or a Kinect) 503. The augmented reality device 501 may include a feedback controller 508 or a display 510. The gesture analyzer device 503 may be in communication with a database 511. The database 511 may include video storage 512 or animation storage 514. In an example, the augmented reality device 501 may be a Holo Lens manufactured by Microsoft of Redmond, Wash.

The processor 502 may be used to receive information about a clinical movement of a therapist, such as a clinical movement captured using the movement capture apparatus 503. The processor 502 may analyze the clinical movement to determine a path of motion of the clinical movement, such as a path of motion on video captured by the movement capture apparatus 503. The processor 502 may automatically define a path region, such as by using the path of motion. The processor 502 may receive information about a movement of a patient along the path of motion, such as movement of the patient captured using the movement capture apparatus 503. The processor 502 may determine whether the movement was within the path region. In an example, the processor 502 may send feedback, such as to the feedback controller 508 or the display 510. The feedback may indicate whether the movement was within the path region. The display 510 may display the feedback, such as by visually indicating (e.g., on a user interface) whether the movement was within or outside the path region or where the movement may have been outside the path region. The feedback controller 508 may be used to send the feedback to the display 510, issue an audible alert, provide haptic feedback, or the like. In an example, the display 510 may be a screen, an augmented reality display, a virtual reality display, or the like.

The processor 502 may determine a start position or an end position automatically for the clinical movement, and the start position or the end position may be included in the path region. For example, to determine whether the movement was within the path region may include determining whether the movement started in the start position or ended in the end position. The display 510 may be used by a therapist (e.g., on a therapist user interface) to modify the path region, the start position, or the end position. The processor 502 may be used to create a video or animation using the path region and the information about the clinical movement. For example, the video may include the path region superimposed on captured video or animation of the clinical movement. The video may be played on the display 510. While playing the video on the display 510, the movement capture apparatus 503 may be used to capture the movement of the patient. The captured video may be stored in the video storage 512. The animation may be stored in the animation storage 514. In an example, a video may be retrieved from the video storage 512. The retrieved video may include an automatically added path region, start position, or end position. In another example, an animation may be retrieved from the animation storage 514. The retrieved animation may include an automatically added path region, start position, or end position.

The processor 502 of the augmented reality device 501 includes an augmented reality modeler 518. The augmented reality device 501 may include a camera 506. The system 500 may include the database 511, which may communicate with the augmented reality device 501.

The processor 502 may identify an object in a real environment, such as through processing information received using the camera 506. For example, the processor 502 may receive information, such as an image or a series of images from the camera 506 and identify in the image or the series of images, the object. The processor 502 may create virtual target (e.g., a line, a bubble, etc.) in an augmented reality (AR) environment. The virtual target may have a fixed position, such as a position fixed with respect to the object. For example, the virtual target may be positioned in the AR environment such that the virtual target remains fixed when the AR device 501 moves. In an example, the virtual target may be fixed without respect to a view presented to a user of the AR device. In an example, the virtual target may be a sphere (e.g. bubble) represented in the real environment in a position fixed with respect to the patient. The patient, for example, may be seated, and instructed to do a leg extension (e.g., knee extension from a flexed position). The sphere may be placed at a final destination for the patient's foot in performing the knee extension (e.g., in front of the patient at an approximate distance the length of the patient's leg at approximately the height of the patient's knee). The sphere may disappear when the patient's foot enters the sphere (or comes close to it). The disappearance of the sphere may indicate a successfully performed movement. In another example, a series of spheres, such as along the path of the foot from the flexed knee position to the extended knee position, may be virtually displayed and disappear as the foot enters each subsequent sphere (which may overlap to show an intended path of movement).

The display 510 may display the AR environment overlaid on the real environment. The display 510 may show the virtual target, using the AR device 501, in the fixed position in the AR environment. In an example, the display 501 may remove the virtual target from display in the AR environment in response to detecting a user interaction with the virtual target. For example, when the virtual target is a line or bubble, the virtual target may be removed (e.g., fade out, popped, explode, etc.) when a user interacts with the virtual target (e.g., kicks the bubble, moves a body part past the line, etc.).

In an example, the camera 506 may be used to identify the object in the real environment. The camera 506 may send information, such as images to the processor 502 about the object, and the processor 502 may use the raw information (e.g., raw images) to identify the object in the real environment. The augmented reality device 501 may include a sensor 516, such as an infrared sensor. In another example, the sensor may be on the object. In an example, the processor 502 may receive information from the sensor 516 on the object to identify the object. The camera 506 or the sensor 516 may be used to detect movement that may be interpreted by the processor 502 as attempted or intended interaction by the user with the virtual target.

The augmented reality modeler 518 may be used by the processor 502 to create the augmented reality environment. For example, the augmented reality modeler 518 may receive dimensions of a room, such as from the camera 506 or sensor 516, and create the augmented reality environment to fit within the physical structure of the room. In another example, physical objects may be present in the room and the augmented reality modeler 518 may use the physical objects to present virtual objects in the augmented reality environment. For example, the augmented reality modeler 518 may use or detect a table present in the room and present a virtual object as resting on the table. In an example, a plurality of physical items may be used by a user to interact with the virtual target. The virtual object may be used by a user to complete a physical therapy movement.

Figure 6:
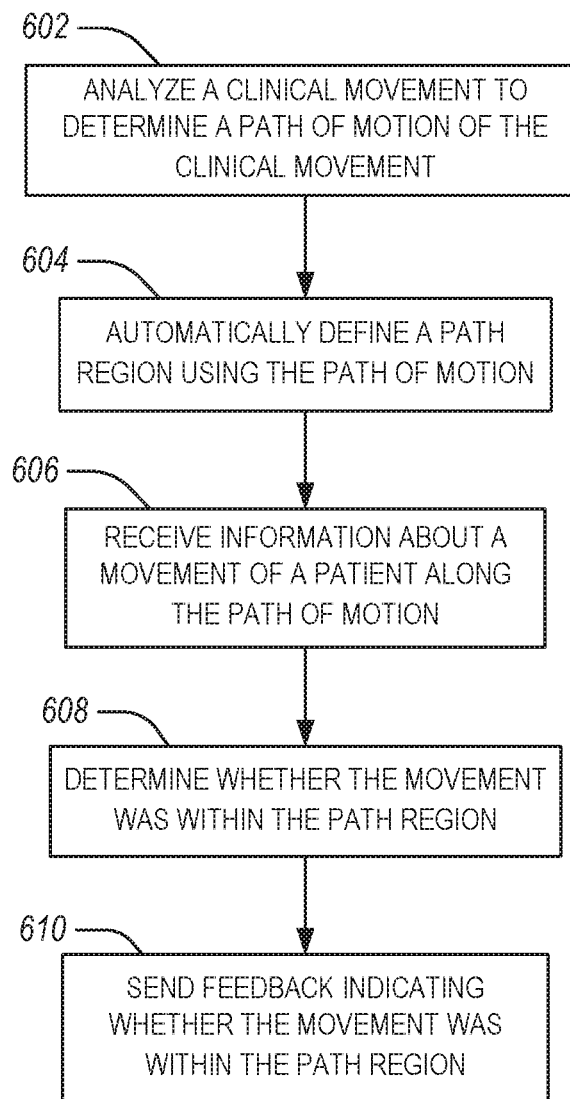
FIG. 6 illustrates a flow chart showing a technique for telerehabilitation in accordance with some embodiments.

FIG. 6 illustrates a flow chart showing a technique 600 for telerehabilitation in accordance with some embodiments. The technique 600 includes an operation 602 to analyze a clinical movement to determine a path of motion of the clinical movement. The clinical movement may be received from a movement capture apparatus that captures the clinical movement, performed by a therapist. To analyze the clinical movement may include determining a start position or an end position.

The technique 600 includes an operation 604 to automatically define a path region using the path of motion. To automatically define the path region may include defining a start region or an end region, such as by using the start position or the end position (e.g., the start region may be an area surrounding the start position, or the end region may be an area surrounding the end position). The start position or the end position may be determined from a limb position of the therapist in a video. In an example, the path region may include a predetermined area surrounding the path of motion. The technique 600 includes an operation 606 to receive information about a movement of a patient along the path of motion. The information may include whether the movement stays within the path of motion, moves outside the path of motion, follows the path of motion (e.g., within a range of error around the path of motion), or the like. In an example, receiving information includes capturing and analyzing video. In an example, receiving information may include analyzing live video of the patient, superimposing the live video on the animation including the path of motion and path region to provide immediate visual feedback to the patient regarding the exercise/gesture being performed.

The technique 600 includes an operation 608 to determine whether the movement was within the path region. To determine whether the movement was within the path region may include determining whether the movement started in the start region or ended in the end region. In an example, determining whether the movement was within the path region includes determining that the movement was outside the path region. In an example, determining whether the movement was within the path region includes determining that the movement was within the path region.

In an example, the technique 600 may include monitoring a patient movement. The patient movement may be compared with the path region to determine whether the movement was within the path region, whether the movement started in the start region, and whether the movement ended in the end region. The technique 600 may include sending feedback comprising a real-time depiction of the movement of the patient. The real-time depiction may include displaying the movement on a display, such as with visual indicators of the start region, the end region, or the path region. For example, a bubble may be used to represent the start region. The path region may be represented by a series of bubbles or visual indicators of edges of the path region. In an example, the real-time depiction of the patient movement includes an animation representing the clinical movement including the path region. In another example, the real-time depiction includes a video of the clinical movement including the path region. The animation or video representing the clinical movement may include a color-coded visual effect to indicate compliance or non-compliance of the patient movement with the clinical movement. For example, the edges of the path region may turn red in response to detecting that the patient has moved outside the path region. The edges may be green when the patient movement is within the path region. The edges may turn yellow when the movement approaches within a specified distance of the edges of the path region. In an example, the start region and the end region may be represented by bubbles, which may be sustained until the patient moves into the start region or the end region. When the patient moves into the start region or the end region, the bubbles may pop. In an example, the path region may be represented by a series of bubbles (e.g., starting after the start region bubble and ending before the end region bubble, along the path of motion). The patient movement through the series of bubbles may pop the series of bubbles in order while completing the movement.

The technique 600 includes an operation 610 to send feedback indicating whether the movement was within the path region. Sending feedback may include providing an alert to the patient or the therapist when the movement was determined to be outside the path region. The feedback may include an indication that the movement is to be repeated. The feedback may include an alert that the patient failed to complete the movement. Sending feedback may include providing an indication to the patient or the therapist that the movement successfully mimicked the clinical movement when the movement falls within the path region. The feedback may include an indication that the patient completed the movement successfully. The feedback may include visual feedback, auditory feedback, haptic feedback, non-contact feedback, or the like. The feedback may be presented on a user interface on a display. The user interface may include an option to modify the path region. The therapist may select a modification to the path region, the start region, or the end region.

In an example, the technique 600 includes creating a video or animation using the path region and the information about the clinical movement. The video or animation may include the path region superimposed on captured video or animation of the clinical movement. The video or animation may be played on a display. In an example, the video or animation may be played on a display while capturing the movement of the patient using the movement capture apparatus. The movement may be displayed on the display.

Figure 7:
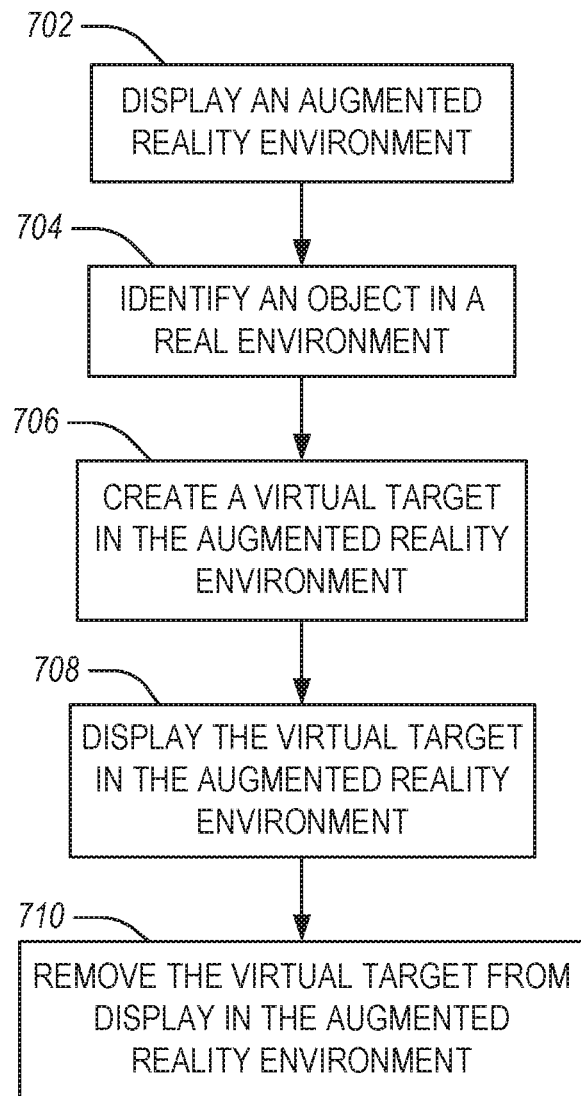
FIG. 7 illustrates a flow chart showing a technique for displaying directions related to a therapeutic movement for a patient within an augmented reality environment in accordance with some embodiments.

FIG. 7 illustrates a flow chart showing a technique 700 for displaying directions related to a therapeutic movement for a patient within an augmented reality environment in accordance with some embodiments. The technique 700 includes an operation 702 to display the augmented reality environment, such as an AR environment overlaid on a real environment. Operation 702 may be performed by an AR device. The AR environment may be created using an augmented reality modeler. The technique 700 includes an operation 704 to identify an object in a real environment. The object may be identified using a camera of an AR device. In an example, the object may be identified using a sensor on the object to identify the object.

The technique 700 includes an operation 706 to create a virtual target in the augmented reality environment. The virtual target may have a fixed position relative to the object in the real environment. The virtual target may be fixed without respect to a view presented to a user of an augmented reality device. For example, the virtual target may remain in a position fixed in the real environment when an AR device moves. The virtual target may be used, for example, by a user to complete a physical therapy movement. Displaying the virtual target in the fixed position may include displaying a bubble, such as in a position at an end of a physical therapy movement to be completed by a user. The bubble may be popped by displaying an animation, in response to user interaction with the bubble (e.g., completion of the therapeutic movement). In an example, displaying the virtual target in the fixed position includes displaying a virtual physical therapy movement using a virtual avatar, the virtual physical therapy movement corresponding to the physical therapy movement to be completed by the user. In an example, the virtual avatar is a virtual representation of a physical therapist.

The technique 700 includes an operation 708 to display the virtual target in the augmented reality environment. The virtual target may be displayed in the fixed position for use in the therapeutic movement in the augmented reality environment by the augmented reality device. The fixed position may be located at an intended starting, ending, or intermediate location of the therapeutic movement. The technique 700 includes an operation 710 to remove the virtual target from display in the augmented reality environment. Operation 710 may include removing the virtual target from display in response to detecting a user interaction with the virtual target, wherein the user indication may indicate completion of the therapeutic movement. To detect the user interaction with the virtual target may include using a camera or a sensor (e.g., a camera or a sensor on an AR device).

The technique 700 may include displaying in the AR environment a plurality of physical items to be used by a user to interact with the virtual target. In an example, the plurality of physical items may be identified in the AR environment, such as with a visual indicator over or near a physical item, or by displaying a virtual representation of the physical item. The technique 700 may include displaying an indication in the augmented reality environment, the indication including clinical information regarding the user interaction.

Figure 8:
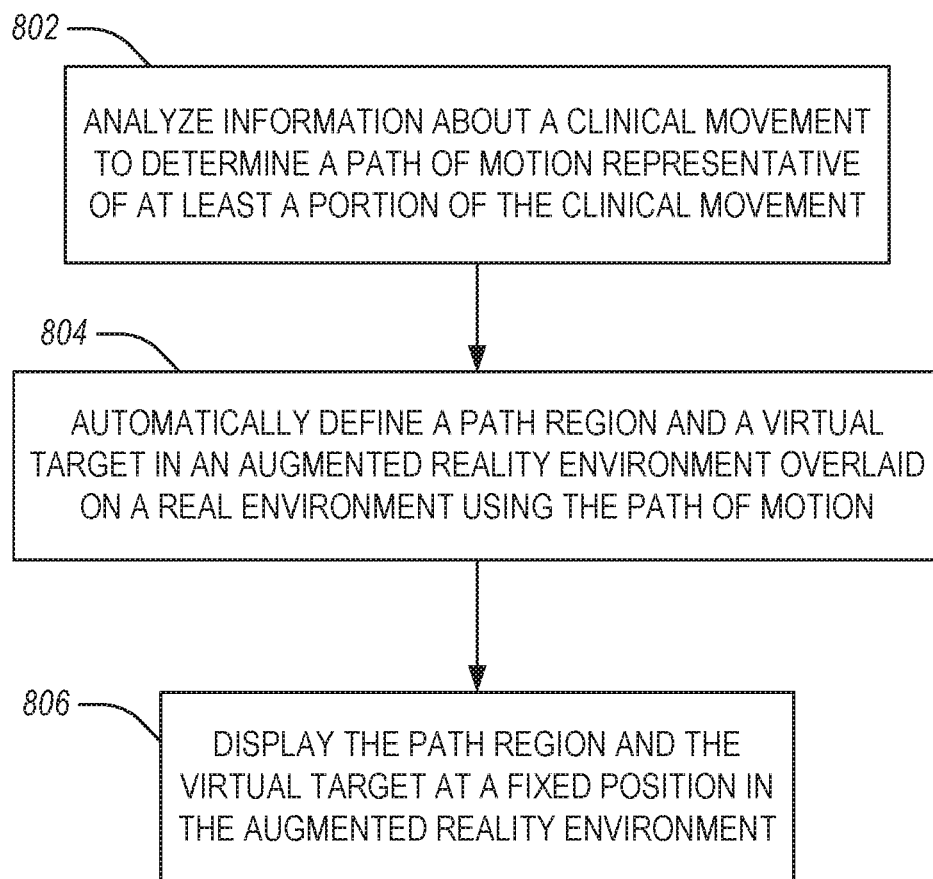
FIG. 8 illustrates a flow chart showing a technique for displaying augmented reality clinical movements in accordance with some embodiments.

FIG. 8 illustrates a flow chart showing a technique for displaying augmented reality clinical movements in accordance with some embodiments. The technique 800 includes an operation 802 to analyze information about a clinical movement, such as a clinical movement by a therapist, to determine a path of motion representative of at least a portion of the clinical movement. In an example, a clinical movement may include a movement for an exercise, a routine, a stretch, an occupational therapy movement, a physical therapy movement, or the like. The clinical movement of the therapist may be captured using a movement capture apparatus. In an example, the movement capture apparatus includes an infrared sensor and the path of motion is determined from a series of snapshots, the snapshots including infrared sensor data from the infrared sensor.

The technique 800 includes an operation 804 to automatically define a path region and a virtual target in an augmented reality environment overlaid on a real environment using the path of motion. The virtual target may have a fixed position relative to an object in the real environment. For example, the virtual target may have a fixed position relative to aspects of a room (e.g., a floor, a wall, a ceiling, etc.), fixtures (e.g., a table, a chair, etc.), moving objects (e.g., a person, a pet, a skateboard, etc.), or the like. In an example, the path region is defined as a region including a specified distance around the path of motion. Operation 804 may include receiving a modification to the path region from the therapist on a user interface of a display.

The technique 800 includes an operation 806 to display the path region and the virtual target at the fixed position in the augmented reality environment. The path region and the virtual target may be displayed using an augmented reality device. In an example, the fixed position may be located at an intended ending location of the path region.

In an example, displaying the virtual target includes displaying a movement task object representative of a real-world object used in occupational or physical therapy. For example, the real-world object may include dishes, and a movement task associated with the dishes may include display a virtual representation of the dishes to be "moved" virtually in the augmented reality environment to mimic the real-world task of putting the dishes away. In another example, the real-world object may be a pet (e.g., a cat or dog), and a real-world task that may be simulated in the augmented reality environment may include stepping over the pet. In yet another example, a box may be augmented to appear as a stair, and the task may include stepping onto the box to simulate climbing a stair. Other examples may include other real-world objects for avoidance, everyday tasks, or the like, for tasks such as stepping on a gas/brake pedal, lifting a cup of coffee, taking a picture, typing, brushing teeth, opening a door, getting into a car, etc.

The augmented reality device may be used to display, in the augmented reality environment, a plurality of physical items to be used in the user interaction with the virtual target. For example, a virtual representation of a weight may be displayed, the weight corresponding to a weight to be lifted in the clinical movement. In another example, a resistance band may be shown, including for example a color, for use in the clinical movement.

In an example, the technique 800 may include displaying an indication in the augmented reality environment, the indication including clinical information regarding a user interaction. For example, the indication may be displayed to the user to indicate that the clinical movement was performed successfully or was not completed. Information displayed to the user may include encouragement or advice (e.g., "lift leg just a little bit more"). In another example, the indication may be displayed to the therapist to update the therapist on a patient's technique, success, failure, progress, exertion level, etc.

While the virtual target is displayed, the user may interact with the virtual target in the augmented reality environment. The user's action in the real environment may trigger an effect in the augmented reality environment. For example, the virtual target may be removed from display in the augmented reality environment in response to detecting a user interaction with the virtual target, such as completion of the clinical movement. Removing the virtual target may indicate completion of the clinical movement. In an example, the user interaction with the virtual target may be detected using a camera, the user interaction causing the virtual target to be removed from the augmented reality environment. For example, the camera and the augmented reality display device may communicate (or communicate with a third device) to determine whether the displayed virtual target overlaid in the real environment and the user interaction in the real environment occupy overlapping space in the real environment.

In an example, the technique 800 includes sending feedback comprising a real-time depiction of movement along the path region toward the virtual target corresponding to a patient movement attempting to reproduce the clinical movement using the augmented reality device. In an example, the real-time depiction of the patient movement includes an animation representing the clinical movement including the path region. For example, the animation representing the clinical movement may be color-coded to indicate compliance or non-compliance of the patient movement with the clinical movement.

In an example, the technique 800 includes receiving information about a movement of a user along the path of motion to the virtual target. The information may be used to determine whether the movement was within the path region, such as based on analysis of the information about the movement of the user. In response to determining that the movement was within the path region, the technique 800 may include displaying, using the augmented reality device, feedback indicating that the movement was within the path region.

In an example, an AR device may be used by a surgeon or a patient postoperatively. For example, the surgeon or the patient may use the AR device to view aspects of an implant or a surgery, such as using an implant sensor, medical imaging (e.g., x-ray, MRI, CT-scan, etc.), or images or video taken during surgery. The AR device may display stored video of the implant or aspects of the surgery postoperatively as a three-dimensional virtual object overlaid on a real environment. The virtual object may be viewed by the surgeon or the patient (or other user), in three-dimensions such that the virtual object appears to be in a room with the surgeon or the patient and the virtual object may be viewed from multiple different angles as the surgeon or the patient moves the AR device around the virtual object. For example, the virtual object may be stationary or may move with one or more points fixed to an aspect of the real environment (e.g., the virtual object may appear to be resting on a table). In an example, the surgeon and the patient may view the virtual object together, and the surgeon may control the virtual object, to show the virtual object moving or may point out certain aspects of the virtual object.

Figure 9:
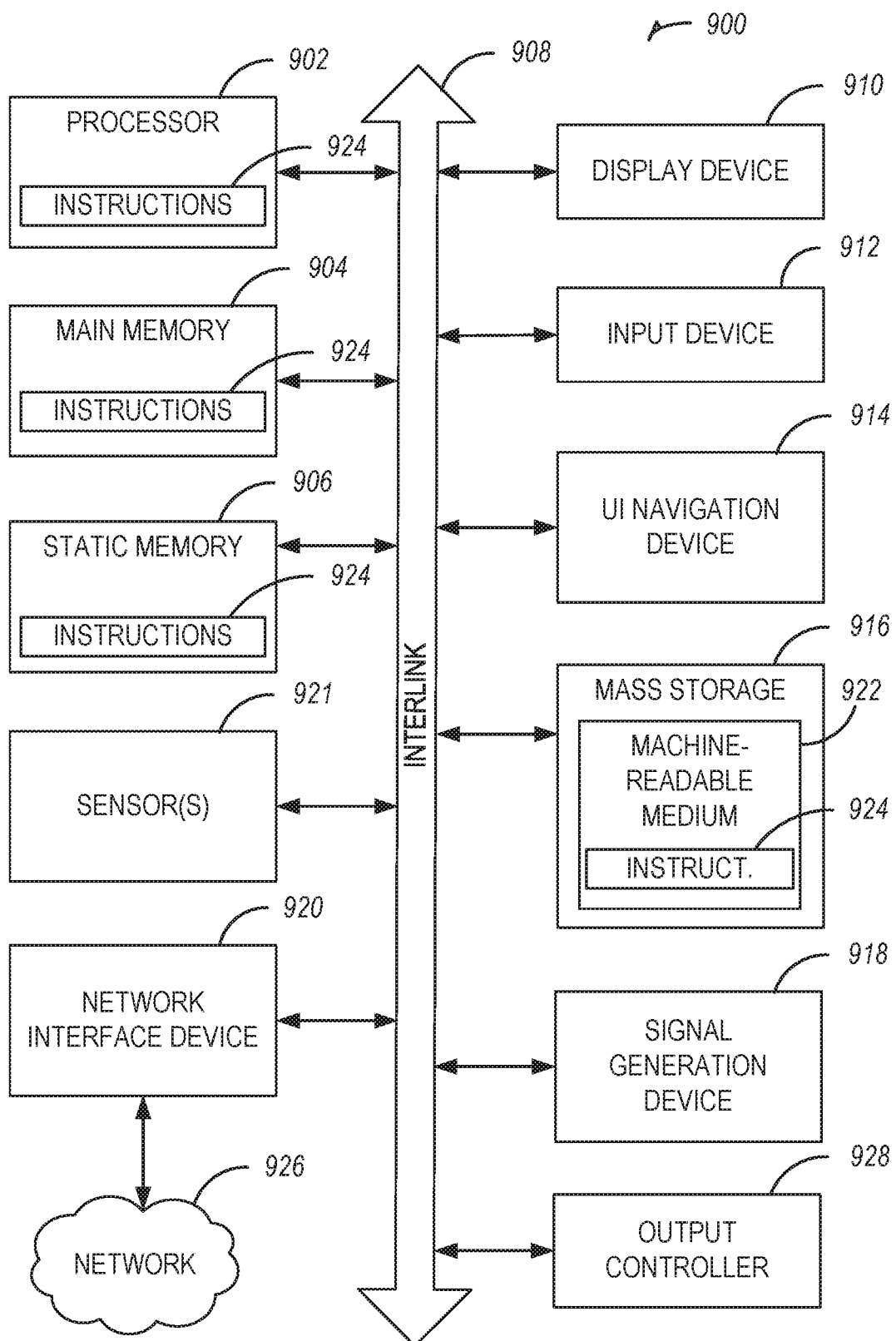
FIG. 9 illustrates generally an example of a block diagram of a machine upon which any one or more of the techniques discussed herein may perform in accordance with some embodiments.

FIG. 9 illustrates generally an example of a block diagram of a machine 900 upon which any one or more of the techniques (e.g., methodologies) discussed herein may perform in accordance with some embodiments. In alternative embodiments, the machine 900 may operate as a standalone device or may be connected (e.g., networked) to other machines. In a networked deployment, the machine 900 may operate in the capacity of a server machine, a client machine, or both in server-client network environments. The machine 900 may be a personal computer (PC), a tablet PC, a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or like mechanisms. Such mechanisms are tangible entities (e.g., hardware) capable of performing specified operations when operating. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the executions units or a loading mechanism. Accordingly, the execution units are communicatively coupled to the computer readable medium when the device is operating. For example, under operation, the execution units may be configured by a first set of instructions to implement a first set of features at one point in time and reconfigured by a second set of instructions to implement a second set of features.

Machine (e.g., computer system) 900 may include a hardware processor 902 (e.g., a central processing unit (CPU), a graphics processing unit (GPU), a hardware processor core, or any combination thereof), a main memory 904 and a static memory 906, some or all of which may communicate with each other via an interlink (e.g., bus) 908. The machine 900 may further include a display unit 910, an alphanumeric input device 912 (e.g., a keyboard), and a user interface (UI) navigation device 914 (e.g., a mouse). In an example, the display unit 910, alphanumeric input device 912 and UI navigation device 914 may be a touch screen display. The display unit 910 may include goggles, glasses, or other AR or VR display components. For example, the display unit may be worn on a head of a user and may provide a heads-up-display to the user. The alphanumeric input device 912 may include a virtual keyboard (e.g., a keyboard displayed virtually in a VR or AR setting.

The machine 900 may additionally include a storage device (e.g., drive unit) 916, a signal generation device 918 (e.g., a speaker), a network interface device 920, and one or more sensors 921, such as a global positioning system (GPS) sensor, compass, accelerometer, or other sensor. The machine 900 may include an output controller 928, such as a serial (e.g., universal serial bus (USB), parallel, or other wired or wireless (e.g., infrared (IR), near field communication (NFC), etc.) connection to communicate or control one or more peripheral devices.

The storage device 916 may include a machine readable medium 922 that is non-transitory on which is stored one or more sets of data structures or instructions 924 (e.g., software) embodying or utilized by any one or more of the techniques or functions described herein. The instructions 924 may also reside, completely or at least partially, within the main memory 904, within static memory 906, or within the hardware processor 902 during execution thereof by the machine 900. In an example, one or any combination of the hardware processor 902, the main memory 904, the static memory 906, or the storage device 916 may constitute machine readable media.

While the machine readable medium 922 is illustrated as a single medium, the term "machine readable medium" may include a single medium or multiple media (e.g., a centralized or distributed database, or associated caches and servers) configured to store the one or more instructions 924.

The term "machine readable medium" may include any medium that is capable of storing, encoding, or carrying instructions for execution by the machine 900 and that cause the machine 900 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 924 may further be transmitted or received over a communications network 926 using a transmission medium via the network interface device 920 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, as the personal area network family of standards known as Bluetooth® that are promulgated by the Bluetooth Special Interest Group, peer-to-peer (P2P) networks, among others. In an example, the network interface device 920 may include one or more physical jacks (e.g., Ethernet, coaxial, or phone jacks) or one or more antennas to connect to the communications network 926. In an example, the network interface device 920 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 900, and includes digital or analog communications signals or other intangible medium to facilitate communication of such software.

VARIOUS NOTES & EXAMPLES

Each of these non-limiting examples may stand on its own, or may be combined in various permutations or combinations with one or more of the other examples.

Example 1 is a method for displaying augmented reality clinical movements, the method comprising: analyzing information about a clinical movement of a therapist, captured using a movement capture apparatus, to determine a path of motion representative of at least a portion of the clinical movement; automatically defining a path region and a virtual target in an augmented reality environment overlaid on a real environment using the path of motion, the virtual target having a fixed position relative to an object in the real environment; and displaying, using an augmented reality device, the path region and the virtual target at the fixed position in the augmented reality environment, the fixed position located at an intended ending location of the path region.

In Example 2, the subject matter of Example 1 optionally includes receiving information about a movement of a user along the path of motion to the virtual target.

In Example 3, the subject matter of Example 2 optionally includes determining, based on analysis of the information about the movement of the user, whether the movement was within the path region, and in response to determining that the movement was within the path region, displaying, using the augmented reality device, feedback indicating that the movement was within the path region.

In Example 4, the subject matter of any one or more of Examples 1-3 optionally include removing the virtual target from display in the augmented reality environment, in response to detecting a user interaction with the virtual target indicating completion of a user movement replicating the clinical movement.

In Example 5, the subject matter of any one or more of Examples 1-4 optionally include wherein the movement capture apparatus includes an infrared sensor and the path of motion is determined from a series of snapshots, the snapshots including infrared sensor data from the infrared sensor.

In Example 6, the subject matter of Example 5 optionally includes wherein the path region is defined as a region including a specified distance around the path of motion.

In Example 7, the subject matter of any one or more of Examples 1-6 optionally include receiving a modification to the path region from the therapist on a user interface of a display.

In Example 8, the subject matter of any one or more of Examples 1-7 optionally include sending feedback comprising a real-time depiction of movement along the path region toward the virtual target corresponding to a patient movement attempting to reproduce the clinical movement using the augmented reality device.

In Example 9, the subject matter of Example 8 optionally includes wherein the real-time depiction of the patient movement includes an animation representing the clinical movement including the path region.

In Example 10, the subject matter of Example 9 optionally includes wherein the animation representing the clinical movement is color-coded to indicate compliance or noncompliance of the patient movement with the clinical movement.

In Example 11, the subject matter of any one or more of Examples 1-10 optionally include displaying, in the augmented reality environment, a plurality of physical items to be used in the user interaction with the virtual target.

In Example 12, the subject matter of any one or more of Examples 1-11 optionally include detecting a user interaction with the virtual target in data received from a camera, the user interaction causing the virtual target to be removed from the augmented reality environment.

In Example 13, the subject matter of any one or more of Examples 1-12 optionally include wherein displaying the virtual target includes displaying a movement task object representative of a real-world object used in occupational therapy.

In Example 14, the subject matter of any one or more of Examples 1-13 optionally include displaying an indication in the augmented reality environment, the indication including clinical information regarding a user interaction.

Example 15 is an augmented reality device for displaying directions related to the clinical movement for a patient within an augmented reality environment comprising: a processor to: analyze information about a clinical movement of a therapist, captured using a movement capture apparatus, to determine a path of motion representative of at least a portion of the clinical movement; and automatically define a path region and a virtual target in an augmented reality environment overlaid on a real environment using the path of motion, the virtual target having a fixed position relative to an object in the real environment; and a display to: display, using an augmented reality device, the path region and the virtual target at the fixed position in the augmented reality environment, the fixed position located at an intended ending location of the path region.

In Example 16, the subject matter of Example 15 optionally includes wherein the processor is further to receive information about a movement of a user along the path of motion to the virtual target.

In Example 17, the subject matter of Example 16 optionally includes wherein the processor is further to determine, based on analysis of the information about the movement of the user, whether the movement was within the path region, and in response to determining that the movement was within the path region, the display is further to display, using the augmented reality device, feedback indicating that the movement was within the path region.

In Example 18, the subject matter of any one or more of Examples 15-17 optionally include wherein the display is further to remove the virtual target from display in the augmented reality environment, in response to detecting a user interaction with the virtual target indicating completion of a user movement replicating the clinical movement.

In Example 19, the subject matter of any one or more of Examples 15-18 optionally include wherein the movement capture apparatus further includes an infrared sensor and the path of motion is determined from a series of snapshots, the snapshots including infrared sensor data from the infrared sensor.

In Example 20, the subject matter of Example 19 optionally includes wherein the path region is defined as a region including a specified distance around the path of motion.

In Example 21, the subject matter of any one or more of Examples 15-20 optionally include wherein the processor is further to receive a modification to the path region from the therapist on a user interface of the display.

In Example 22, the subject matter of any one or more of Examples 15-21 optionally include wherein the processor is further to generate feedback comprising a real-time depiction of movement along the path region toward the virtual target corresponding to a patient movement attempting to reproduce the clinical movement using the augmented reality device.

In Example 23, the subject matter of Example 22 optionally includes wherein the real-time depiction of the patient movement includes an animation representing the clinical movement including the path region.

In Example 24, the subject matter of Example 23 optionally includes wherein the animation representing the clinical movement is color-coded to indicate compliance or noncompliance of the patient movement with the clinical movement.

In Example 25, the subject matter of any one or more of Examples 15-24 optionally include wherein the display is further to display, in the augmented reality environment, a plurality of physical items to be used in the user interaction with the virtual target.

In Example 26, the subject matter of any one or more of Examples 15-25 optionally include wherein the processor is further to detect a user interaction with the virtual target in data received from a camera, the user interaction causing the virtual target to be removed from the augmented reality environment.

In Example 27, the subject matter of any one or more of Examples 15-26 optionally include wherein to display the virtual target, the display is further to display a movement task object representative of a real-world object used in occupational therapy.

In Example 28, the subject matter of any one or more of Examples 15-27 optionally include wherein the display is further to display an indication in the augmented reality environment, the indication including clinical information regarding a user interaction.

Example 29 is a system comprising: a movement capture apparatus including a camera to capture information about a clinical movement of a therapist; and a processor to: analyze the information to determine a path of motion representative of at least a portion of the clinical movement; and automatically define a path region and a virtual target in an augmented reality environment overlaid on a real environment using the path of motion, the virtual target having a fixed position relative to an object in the real environment; and an augmented reality display device to display the path region and the virtual target at the fixed position in the augmented reality environment, the fixed position located at an intended ending location of the path region.

In Example 30, the subject matter of Example 29 optionally includes a camera to capture information about a movement of a user along the path of motion to the virtual target.

In Example 31, the subject matter of Example 30 optionally includes wherein the processor is further to determine, based on analysis of the information about the movement of the user, whether the movement was within the path region, and in response to determining that the movement was within the path region, the augmented reality display device is further to display feedback indicating that the movement was within the path region.

In Example 32, the subject matter of any one or more of Examples 29-31 optionally include wherein the augmented reality display device is further to remove the virtual target from display in the augmented reality environment, in response to detecting a user interaction with the virtual target indicating completion of a user movement replicating the clinical movement.

In Example 33, the subject matter of any one or more of Examples 29-32 optionally include wherein the movement capture apparatus further includes an infrared sensor and the path of motion is determined from a series of snapshots, the snapshots including infrared sensor data from the infrared sensor.

In Example 34, the subject matter of Example 33 optionally includes wherein the path region is defined as a region including a specified distance around the path of motion.

In Example 35, the subject matter of any one or more of Examples 29-34 optionally include wherein the processor is further to receive a modification to the path region from the therapist on a user interface of the augmented reality display device.

In Example 36, the subject matter of any one or more of Examples 29-35 optionally include wherein the processor is further to generate feedback comprising a real-time depiction of movement along the path region toward the virtual target corresponding to a patient movement attempting to reproduce the clinical movement using the augmented reality device.

In Example 37, the subject matter of Example 36 optionally includes wherein the real-time depiction of the patient movement includes an animation representing the clinical movement including the path region.

In Example 38, the subject matter of Example 37 optionally includes wherein the animation representing the clinical movement is color-coded to indicate compliance or non-compliance of the patient movement with the clinical movement.

In Example 39, the subject matter of any one or more of Examples 29-38 optionally include wherein the augmented reality display device is further to display, in the augmented reality environment, a plurality of physical items to be used in the user interaction with the virtual target.

In Example 40, the subject matter of any one or more of Examples 29-39 optionally include wherein the processor is further to detect a user interaction with the virtual target in data received from a camera, the user interaction causing the virtual target to be removed from the augmented reality environment.

In Example 41, the subject matter of any one or more of Examples 29-40 optionally include wherein to display the virtual target, the augmented reality display device is further to display a movement task object representative of a real-world object used in occupational therapy.

In Example 42, the subject matter of any one or more of Examples 29-41 optionally include wherein the augmented reality display device is further to display an indication in the augmented reality environment, the indication including clinical information regarding a user interaction.

Example 43 is at least one machine-readable medium including instructions for displaying augmented reality clinical movements, which when executed by a machine, cause the machine to: analyze information about a clinical movement of a therapist, captured using a movement capture apparatus, to determine a path of motion representative of at least a portion of the clinical movement; automatically define a path region and a virtual target in an augmented reality environment overlaid on a real environment using the path of motion, the virtual target having a fixed position relative to an object in the real environment; and display, using an augmented reality device, the path region and the virtual target at the fixed position in the augmented reality environment, the fixed position located at an intended ending location of the path region.

In Example 44, the subject matter of Example 43 optionally includes instructions to receive information about a movement of a user along the path of motion to the virtual target.

In Example 45, the subject matter of Example 44 optionally includes instructions to determine, based on analysis of the information about the movement of the user, whether the movement was within the path region, and in response to determining that the movement was within the path region, display, using the augmented reality device, feedback indicating that the movement was within the path region.

In Example 46, the subject matter of any one or more of Examples 43-45 optionally include instructions to remove the virtual target from display in the augmented reality environment, in response to detecting a user interaction with the virtual target indicating completion of a user movement replicating the clinical movement.

In Example 47, the subject matter of any one or more of Examples 43-46 optionally include wherein the movement capture apparatus includes an infrared sensor and the path of motion is determined from a series of snapshots, the snapshots including infrared sensor data from the infrared sensor.

In Example 48, the subject matter of Example 47 optionally includes wherein the path region is defined as a region including a specified distance around the path of motion.

In Example 49, the subject matter of any one or more of Examples 43-48 optionally include instructions to receive a modification to the path region from the therapist on a user interface of a display.

In Example 50, the subject matter of any one or more of Examples 43-49 optionally include instructions to generate feedback comprising a real-time depiction of movement along the path region toward the virtual target corresponding to a patient movement attempting to reproduce the clinical movement using the augmented reality device.

In Example 51, the subject matter of Example 50 optionally includes wherein the real-time depiction of the patient movement includes an animation representing the clinical movement including the path region.

In Example 52, the subject matter of Example 51 optionally includes wherein the animation representing the clinical movement is color-coded to indicate compliance or non-compliance of the patient movement with the clinical movement.

In Example 53, the subject matter of any one or more of Examples 43-52 optionally include instructions to display, in the augmented reality environment, a plurality of physical items to be used in the user interaction with the virtual target.

In Example 54, the subject matter of any one or more of Examples 43-53 optionally include instructions to detect a user interaction with the virtual target in data received from a camera, the user interaction causing the virtual target to be removed from the augmented reality environment.

In Example 55, the subject matter of any one or more of Examples 43-54 optionally include wherein the instructions to display the virtual target include instructions to display a movement task object representative of a real-world object used in occupational therapy.

In Example 56, the subject matter of any one or more of Examples 43-55 optionally include instructions to display an indication in the augmented reality environment, the indication including clinical information regarding a user interaction.

Example 57 is a method for telerehabilitation, the method comprising: receiving information about a clinical movement of a therapist captured using a movement capture apparatus; analyzing the clinical movement to determine a path of motion representative of at least a portion of the clinical movement; automatically defining a path region using the path of motion; receiving information about a movement of a patient along the path of motion; determining, based on analysis of the information about the movement of the patient, whether the movement was within the path region; and sending feedback indicating whether the movement was within the path region.

In Example 58, the subject matter of Example 57 optionally includes wherein analyzing the clinical movement includes determining a start position and an end position of the clinical movement.

In Example 59, the subject matter of Example 58 optionally includes wherein automatically defining the path region includes automatically defining a start region and an end region using the start position and the end position.

In Example 60, the subject matter of Example 59 optionally includes wherein determining whether the movement was within the path region includes determining whether the movement started in the start region and ended in the end region.

In Example 61, the subject matter of any one or more of Examples 57-60 optionally include wherein the movement capture apparatus includes an infrared sensor and the path of motion is determined from a series of snapshots, the snapshots including infrared sensor data from the infrared sensor.

In Example 62, the subject matter of Example 61 optionally includes wherein the path region is defined as a region including a specified distance around the path of motion.

In Example 63, the subject matter of any one or more of Examples 57-62 optionally include wherein the path region includes a predetermined area surrounding the path of motion.

In Example 64, the subject matter of any one or more of Examples 57-63 optionally include wherein determining whether the movement was within the path region includes determining that the movement was outside the path region.

In Example 65, the subject matter of Example 64 optionally includes wherein sending the feedback includes providing an alert to the patient that the movement was outside the path region and that the movement is to be repeated.

In Example 66, the subject matter of any one or more of Examples 64-65 optionally include wherein sending the feedback includes providing an alert to the therapist that the patient failed to complete the movement.

In Example 67, the subject matter of any one or more of Examples 57-66 optionally include wherein determining whether the movement was within the path region includes determining that the movement was within the path region.

In Example 68, the subject matter of Example 67 optionally includes wherein sending the feedback includes providing an indication to the patient that the movement successfully mimicked the clinical movement.

In Example 69, the subject matter of any one or more of Examples 67-68 optionally include wherein sending the feedback includes providing an indication to the therapist that the patient completed the movement successfully.

Example 70 is at least one machine-readable medium including instructions for receiving information, which when executed by a machine, cause the machine to: receive information about a clinical movement of a therapist captured using a movement capture apparatus; analyze the clinical movement to determine a path of motion of the clinical movement; automatically define a path region using the path of motion; receive information about a movement of a patient along the path of motion; determine whether the movement was within the path region; and send feedback indicating whether the movement was within the path region.

In Example 71, the subject matter of Example 70 optionally includes wherein the feedback is visual, auditory, or haptic.

In Example 72, the subject matter of any one or more of Examples 70-71 optionally include instructions to receive a modification to the path region from the therapist on a user interface of a display.

In Example 73, the subject matter of any one or more of Examples 70-72 optionally include instructions to create a video using the path region and the information about the clinical movement, the video including the path region superimposed on captured video of the clinical movement.

In Example 74, the subject matter of Example 73 optionally includes instructions to play the video on a display while capturing the movement of the patient using the movement capture apparatus.

Example 75 is a system comprising: a movement capture apparatus; memory; and a processor connected to the memory, the processor to: receive information about a clinical movement performed by a therapist and captured using the movement capture apparatus; analyze the clinical movement to determine a path of motion of the clinical movement; automatically define a path region using the path of motion; receive information about a movement of a patient along the path of motion, the information generated by the movement capture apparatus; determine whether the movement was within the path region; and send feedback indicating whether the movement was within the path region.

In Example 76, the subject matter of Example 75 optionally includes wherein to automatically define the path region, the processor is further to automatically define a start region and an end region using a start position and an end position.

In Example 77, the subject matter of Example 76 optionally includes wherein to determine whether the movement was within the path region, the processor is further to determine whether the movement started in the start region and ended in the end region.

In Example 78, the subject matter of any one or more of Examples 75-77 optionally include wherein the processor is to generate feedback comprising a real-time depiction of the movement of the patient.

In Example 79, the subject matter of Example 78 optionally includes wherein the real-time depiction of the patient movement includes an animation representing the clinical movement including the path region.

In Example 80, the subject matter of any one or more of Examples 78-79 optionally include wherein the animation representing the clinical movement is color-coded to indicate compliance or non-compliance of the patient movement with the clinical movement.

Example 81 is a method for displaying directions related to a therapeutic movement for a patient within an augmented reality environment, the method comprising: displaying the augmented reality environment overlaid on a real environment using an augmented reality device; identifying an object in the real environment; creating a virtual target in the augmented reality environment with a fixed position relative to the object; displaying, using the augmented reality device, the virtual target in the fixed position for use in the therapeutic movement in the augmented reality environment, the fixed position located at an intended ending location of the therapeutic movement; and removing the virtual target from display in the augmented reality environment, in response to detecting a user interaction with the virtual target indicating completion of a user movement replicating the therapeutic movement.

In Example 82, the subject matter of Example 81 optionally includes displaying, in the augmented reality environment, a plurality of physical items to be used in the user interaction with the virtual target.

In Example 83, the subject matter of any one or more of Examples 81-82 optionally include wherein displaying the virtual target in the fixed position includes displaying a bubble in the intended ending location.

In Example 84, the subject matter of Example 83 optionally includes wherein removing the virtual target includes displaying an animation popping the bubble.

In Example 85, the subject matter of any one or more of Examples 81-84 optionally include wherein the virtual target is fixed relative to the object and without respect to a view presented to a user of the augmented reality device.

In Example 86, the subject matter of any one or more of Examples 81-85 optionally include wherein identifying the object in the real environment includes using a camera of the augmented reality device.

In Example 87, the subject matter of any one or more of Examples 81-86 optionally include wherein identifying the object in the real environment includes using a sensor on the object to identify the object.

In Example 88, the subject matter of any one or more of Examples 81-87 optionally include using an augmented reality modeler to create the augmented reality environment.

In Example 89, the subject matter of any one or more of Examples 81-88 optionally include wherein detecting the user interaction with the virtual target includes using a camera.

In Example 90, the subject matter of any one or more of Examples 81-89 optionally include wherein displaying the virtual target in the fixed position includes displaying a virtual physical therapy movement using a virtual avatar, the virtual physical therapy movement corresponding to the physical therapy movement to be completed by the user.

In Example 91, the subject matter of Example 90 optionally includes wherein the virtual avatar is a virtual representation of a physical therapist.

In Example 92, the subject matter of any one or more of Examples 81-91 optionally include displaying an indication in the augmented reality environment, the indication including clinical information regarding the user interaction.

Example 93 is an augmented reality device for displaying directions related to a therapeutic movement for a patient within an augmented reality environment, the augmented reality device comprising: a processor to: identify an object in a real environment; and create a virtual target in an augmented reality environment with a fixed position relative to the object; and a display to: display the augmented reality environment overlaid on the real environment; display, using the augmented reality device, the virtual target in the fixed position for use in the therapeutic movement in the augmented reality environment, the fixed position located at an intended ending location of the therapeutic movement; and remove the virtual target from display in the augmented reality environment, in response to detecting a user interaction with the virtual target indicating completion of a user movement replicating the therapeutic movement.

In Example 94, the subject matter of Example 93 optionally includes wherein the virtual target is fixed without respect to a view presented to a user of the augmented reality device.

In Example 95, the subject matter of any one or more of Examples 93-94 optionally include a camera to identify the object in the real environment.

In Example 96, the subject matter of any one or more of Examples 93-95 optionally include wherein to identify the object in the real environment, the processor is further to receive information from a sensor on the object to identify the object.

In Example 97, the subject matter of any one or more of Examples 93-96 optionally include wherein the processor is further to use an augmented reality modeler to create the augmented reality environment.

In Example 98, the subject matter of any one or more of Examples 93-97 optionally include a camera to detect the user interaction with the virtual target.

In Example 99, the subject matter of any one or more of Examples 93-98 optionally include wherein the display is further to display, in the augmented reality environment, a plurality of physical items to be used by a user to interact with the virtual target.

In Example 100, the subject matter of any one or more of Examples 93-99 optionally include wherein the virtual target is used by a user to complete a physical therapy movement.

In Example 101, the subject matter of any one or more of Examples 1-99 may optionally include a technique or system including display components to allow a therapist to select an object and place the object in an AR environment.

In Example 102, the subject matter of Example 101 may optionally include generating feedback when a user interaction with the placed object is detected.

In Example 103, the subject matter of any one or more of Examples 101-102 optionally include wherein detecting a user interaction with the placed object includes receiving data from a camera, the user interaction causing the placed object to be removed from the AR environment.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A method for evaluating clinical movements, the method comprising:
receiving clinical movement data indicative of a clinical movement of a therapist, the clinical movement data captured using a movement capture apparatus;
analyzing the clinical movement data to determine a three-dimensional path of motion representative of a portion of the clinical movement;

automatically defining a three-dimensional path region using the three-dimensional path of motion;

creating an animation of the portion of the clinical movement including a visual representation of the three-dimensional path region;

displaying the animation including the visual representation of the three-dimensional path region;

receiving patient movement data indicative of a movement of a patient along the three-dimensional path of motion;

determining, based on analysis of the patient movement data about the movement of the patient, whether the movement was within the three-dimensional path region; and sending feedback indicating whether the movement was within the three-dimensional path region.

2. The method of claim 1, wherein analyzing the clinical movement data includes determining a start position and an end position of the clinical movement, wherein automatically defining the three-dimensional path region includes automatically defining a start region and an end region using the start position and the end position, and wherein determining whether the movement was within the three-dimensional path region includes determining whether the movement started in the start region and ended in the end region.

3. The method of claim 1, wherein receiving the clinical movement data includes receiving a plurality of snapshots from the movement capture apparatus that includes an infrared sensor; and wherein analyzing the clinical movement data to determine the three-dimensional path of motion analyzing the plurality of snapshots including infrared sensor data from the infrared sensor.

4. The method of claim 1, wherein defining the three-dimensional path region includes defining a specified distance around the three-dimensional path of motion.

5. The method of claim 1, wherein determining whether the movement was within the three-dimensional path region includes determining that the movement was outside the three-dimensional path region.

6. The method of claim 5, wherein sending the feedback includes providing an alert to the patient that the movement was outside the three-dimensional path region and that the movement is to be repeated.

7. The method of claim 5, wherein sending the feedback includes providing an alert to the therapist that the patient failed to complete the movement.

8. The method of claim 1, wherein determining whether the movement was within the three-dimensional path region includes determining that the movement was within the three-dimensional, path region, and wherein sending the feedback includes providing an indication to the patient that the movement successfully mimicked the clinical movement or providing an indication to the therapist that the patient completed the movement successfully.

9. The method of claim 1, further comprising receiving a modification to the three-dimensional path region from the therapist on a user interface of a display.

10. The method of claim 1, wherein the visual representation of the three-dimensional path region is color-coded within the animation of the portion of the clinical movement to indicate compliance or non-compliance of the movement of the patient with the clinical movement.

11. At least one machine-readable medium including instructions for receiving information, which when executed by a machine, cause the machine to:

receive clinical movement data indicative of a clinical movement of a therapist, the clinical movement data captured using a movement capture apparatus;

analyze the clinical movement data to determine a three-dimensional path of motion representative of a portion of the clinical movement;

automatically define a three-dimensional path region using the three-dimensional path of motion;

create an animation of the portion of the clinical movement including a visual representation of the three-dimensional path region;

cause the animation to be displayed including the visual representation of the three-dimensional path region;

receive patient movement data indicative of a movement of a patient along the three-dimensional path of motion;

determine, based on analysis of the patient movement data about the movement of the patient, whether the movement was within the three-dimensional path region; and send feedback indicating whether the movement was within the three-dimensional path region.

12. The at least one machine-readable medium of claim 11, wherein to analyze the clinical movement data, the instructions are further to cause the machine to determine a start position and an end position of the clinical movement, wherein to automatically define the three-dimensional path region, the instructions are further to cause the machine to automatically define a start region and an end region using the start position and the end position, and wherein to determine whether the movement was within the three-dimensional path region, the instructions are further to cause the machine to determining whether the movement started in the start region and ended in the end region.

13. The at least one machine-readable medium of claim 11, wherein to define the three-dimensional path region, the instructions are further to cause the machine to define a specified distance around the three-dimensional path of motion.

14. The at least one machine-readable medium of claim 11, wherein the visual representation of the three-dimensional path region is color-coded within the animation of the portion of the clinical movement to indicate compliance or non-compliance of the movement of the patient with the clinical movement.

15. The at least one machine-readable medium of claim 11, wherein to send the feedback, the instructions are further to cause the machine to provide an alert to the patient that the movement was outside the three-dimensional path region and that the movement is to be repeated or provide an alert to the therapist that the patient failed to complete the movement.

16. A system comprising:

a display device;

memory; and a processor connected to the memory, the processor to:

receive clinical movement data indicative of a clinical movement of a therapist, the clinical movement data captured using a movement capture apparatus;

analyze the clinical movement data to determine a three-dimensional path of motion representative of a portion of the clinical movement;

automatically define a three-dimensional path region using the three-dimensional path of motion;

create an animation of the portion of the clinical movement including a visual representation of the three-dimensional path region;

send the animation to be displayed on the display device, including the visual representation of the three-dimensional path region;

receive patient movement data indicative of a movement of a patient along the three-dimensional path of motion;

determine, based on analysis of the patient movement data the movement of the patient, whether the movement was within the three-dimensional path region; and send feedback indicating whether the movement was within the three-dimensional path region.

17. The system of claim 16, wherein to determine whether the movement was within the three-dimensional path region, the processor is further to determine that the movement was within the three-dimensional path region, and wherein to send the feedback, the processor is further to provide an indication to the patient that the movement successfully mimicked the clinical movement or provide an indication to the therapist that the patient completed the movement successfully.

18. The system of claim 16, wherein the processor is further to receive a modification to the three-dimensional path region from the therapist on a user interface of a display.

19. The system of claim 16, wherein the visual representation of the three-dimensional path region is color-coded within the animation of the portion of the clinical movement to indicate compliance or non-compliance of the movement of the patient with the clinical movement.

20. The system of claim 16, wherein the system further comprises the movement capture apparatus, including an infrared sensor, the infrared sensor to capture a series of snapshots including infrared sensor data to be used to determine the three-dimensional path of motion.

* * * * *

UNITED STATES PATENT AND TRADEMARK OFFICE
CERTIFICATE OF CORRECTION

PATENT NO. : 10,572,733 B2
APPLICATION NO. : 15/803515
DATED : February 25, 2020
INVENTOR(S) : Wells et al.

It is certified that error appears in the above-identified patent and that said Letters Patent is hereby corrected as shown below:

In the Claims

In Column 31, Line 52, in Claim 8, delete "three-dimensional," and insert --three-dimensional-- therefor Signed and Sealed this
Second Day of May, 2023

Katherine Kelly Vidal
*Director of the United States Patent and Trademark Office*